US012564669B2

(12) United States Patent
Nagel et al.

(10) Patent No.: US 12,564,669 B2
(45) Date of Patent: Mar. 3, 2026

(54) AMBULATORY FLUID DRAINAGE AND COLLECTION DEVICE

(71) Applicant: The Cleveland Clinic Foundation, Cleveland, OH (US)

(72) Inventors: Sean Nagel, Cleveland Heights, OH (US); Sergey Samorezov, Highland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 800 days.

(21) Appl. No.: 17/972,899

(22) Filed: Oct. 25, 2022

(65) Prior Publication Data

US 2024/0131245 A1    Apr. 25, 2024
US 2024/0226409 A9    Jul. 11, 2024

(51) Int. Cl.
*A61M 1/00*      (2006.01)
*A61M 27/00*      (2006.01)
*A61M 39/22*      (2006.01)

(52) U.S. Cl.
CPC .............. *A61M 1/743* (2021.05); *A61M 1/84* (2021.05); *A61M 27/006* (2013.01);
(Continued)

(58) Field of Classification Search
CPC ...... A61M 1/743; A61M 1/84; A61M 27/006; A61M 39/227; A61M 2039/226; A61M 2202/0464; A61M 1/82; A61M 2209/088; A61M 1/80; A61M 1/75; A61M 39/223; A61M 5/16881; A61M 1/81;
(Continued)

(56) References Cited

U.S. PATENT DOCUMENTS 4,431,425 A *   2/1984   Thompson .......... G01P 13/0086
                                  604/245
4,607,596 A     8/1986   Whittlestone
(Continued)

FOREIGN PATENT DOCUMENTS

WO      2021248035      12/2021

OTHER PUBLICATIONS

International Search Report and Written Opinion for PCT/US2022/047683, dated Jun. 30, 2023, 14 pages.

*Primary Examiner* — Nicholas J. Weiss
*Assistant Examiner* — Brandon W. Levy
(74) *Attorney, Agent, or Firm* — Tucker Ellis LLP

(57) ABSTRACT

A valve assembly for controlled drainage or delivery of a fluid from or to a patient including an outlet, an inlet, a diaphragm chamber and a diaphragm dividing the diaphragm chamber into a first chamber cavity and a second chamber cavity. The diaphragm being deflectable toward a first wall of the diaphragm chamber wherein the first chamber cavity contracts and the second chamber cavity expands, and oppositely toward a second wall of the diaphragm chamber wherein the second chamber cavity contracts and the first chamber cavity expands. A plunger is translatable between a first actuation state that establishes fluid communication between the outlet and the second chamber cavity, and separately between the inlet and the first chamber cavity. The valve also having a second actuation state that establishes fluid communication between the outlet and the first chamber cavity, and separately between the inlet and the second chamber cavity.

23 Claims, 14 Drawing Sheets

(52) U.S. Cl.
CPC ..... *A61M 39/227* (2013.01); *A61M 2039/226* (2013.01); *A61M 2202/0464* (2013.01)

(58) Field of Classification Search
CPC .... A61M 2039/224; A61M 2039/2473; A61B 2217/005; A61B 2217/007; A61B 5/031; F04B 45/047; F04B 53/16; F04B 53/10; F04B 49/03; F04B 43/0733; F04B 43/0736; F16K 11/07; F16K 27/041
See application file for complete search history.

(56) References Cited

U.S. PATENT DOCUMENTS

| 7,470,266 | B2 | 12/2008 | Massengale et al. |
| 9,662,478 | B2 | 5/2017 | Browd et al. |
| 2020/0129751 | A1* | 4/2020 | Malkowski ......... A61M 3/0237 |

* cited by examiner

AMBULATORY FLUID DRAINAGE AND COLLECTION DEVICE

FIELD OF THE INVENTION

The present invention relates to a system for ambulatory cerebrospinal fluid (CSF) drainage and collection, and more particularly, to a portable device for regulating the flow of CSF from a patient.

BACKGROUND OF INVENTION

Normal Pressure Hydrocephalus (NPH) is a neurological disorder that afflicts an estimated 750,000 Americans. In NPH, the ventricles in the brain expand with cerebrospinal fluid (CSF) that is not cleared away, compressing surrounding brain tissue. This can cause debilitating symptoms such as impaired gait, urinary urgency and later incontinence, and cognitive decline. The only known treatment for NPH is a surgical intervention called a shunt: a catheter inserted through the skull and into the ventricles and then routed under the skin to another site of the body, typically the abdominal cavity or venous system. The shunt facilitates continuous drainage of excess fluid, which leads to abatement of symptoms.

In order to determine if a patient should receive a shunt (i.e. if such treatment will be beneficial and abate symptoms), multiple tests are performed. At many sites, patients are trialed by draining CSF from the lumbar spine, which removes CSF and is intended to simulate the shunt. This can be done either as a discrete, one time spinal tap trial (outpatient) or an inpatient multi-day test with a temporary catheter.

An outpatient lumbar tap test includes only a very short simulation of drainage under controlled conditions. Usually 25-50 ml of CSF is removed. Inpatient tests require the patient to be immobilized, and a nurse to attend to the patient during drainage, consuming valuable healthcare resources. During inpatient drainage trials, several hundred milliliters of fluid can be removed.

It is desirable to provide a portable device that facilitates substantially continuous CSF drainage over a period of time. Such a device will better simulate the performance and effect of an implanted shunt, while leaving the patient free to ambulate and resume normal activities, unconfined to a healthcare facility.

SUMMARY OF INVENTION

There is provided a valve assembly for controlled drainage or delivery of a fluid from or to a patient. The valve assembly including an inlet, an outlet, a diaphragm chamber and a diaphragm dividing the diaphragm chamber into a first chamber cavity and a second chamber cavity. The diaphragm being deflectable toward a first wall of the diaphragm chamber wherein the first chamber cavity contracts and the second chamber cavity expands, and oppositely toward a second wall of the diaphragm chamber wherein the second chamber cavity contracts and the first chamber cavity expands. A valve is actuatable between a first actuation state that establishes fluid communication between the inlet and the second chamber cavity, and separately between the outlet and the first chamber cavity. The valve also having a second actuation state that establishes fluid communication between the inlet and the first chamber cavity, and separately between the outlet and the second chamber cavity. The first chamber cavity and the second chamber cavity being fluidically isolated from one another in all actuation states of the valve.

There is further provided a valve assembly for controlled drainage or delivery of a fluid from or to a patient. The valve assembly including a diaphragm disposed in a diaphragm chamber and dividing the diaphragm chamber into a first chamber cavity and a second chamber cavity. The diaphragm being deflectable toward a first wall of the diaphragm chamber to contract the first chamber cavity and expand the second chamber cavity, and oppositely toward a second wall of the diaphragm chamber to contract the second chamber cavity and expand the first chamber cavity. A valve body includes a central chamber. An inlet passage fluidly connects the central chamber to an inlet of the valve body. An outlet passage fluidly connects the central chamber to an outlet of the valve body. A first chamber passage fluidly connects the central chamber to the first chamber cavity. A second chamber passage fluidly connects the central chamber to the second chamber cavity. A plug is disposed in the central chamber and is actuatable between a first actuation state that establishes fluid communication between the inlet passage and the second chamber passage, and separately between the outlet passage and the first chamber passage. The plug also having a second actuation state that establishes fluid communication between the inlet passage and the first chamber passage, and separately between the outlet passage and the second chamber passage. The first chamber cavity and the second chamber cavity being fluidically isolated from one another in all actuation states of the plug.

A portable ambulatory fluid drainage or delivery device, which includes a pump assembly attachable to a patient. The pump assembly includes a pump that is actuatable to pump fluid, a motor operative to actuate the pump, a first port and a second port each in fluid communication with the pump, and a controller adapted to operate the motor in order to regulate actuation of the pump to pump fluid at a controlled rate. A reservoir cartridge is removably installable to the pump assembly and includes a reservoir that is placed in communication with the second port upon installation of said reservoir cartridge to the pump assembly. The reservoir cartridge has a reservoir for holding fluid. With the cartridge installed to the pump assembly, the device fits within a form-factor envelope having overall dimensions no greater than about 500 mm by about 200 mm by about 100 mm.

DETAILED DESCRIPTION OF PREFERRED EMBODIMENT

As used herein, relative terms of orientation such as "upper" and "lower" are used merely to distinguish one component or part of a component from another component or part of a component. Such terms are not meant to denote a preference or a particular orientation, and are not meant to limit embodiments of the present invention. For example, an 'upper' element may be positionally located next to the 'lower' element as herein disclosed depending on the spatial orientation of that component comprising those elements in real space. Or those 'upper' and 'lower' elements in fact may even be inverted if the component comprising them is inverted.

Figure 1:
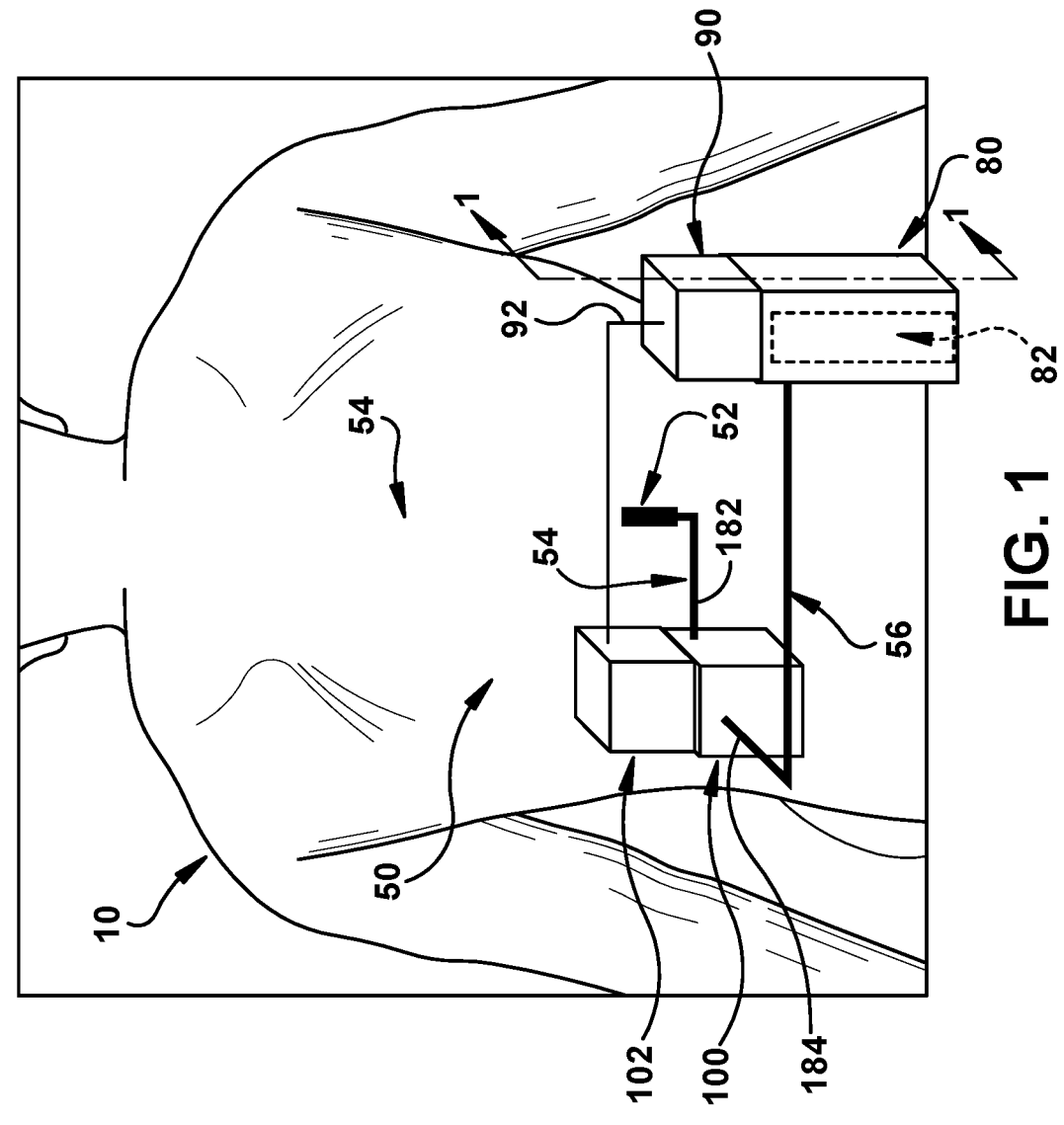
FIG. 1 is schematic view of a drainage system as disclosed herein in-use on a patient.

Referring to the drawings, FIG. 1 schematically shows an ambulatory CSF drainage system 50 that can be carried by a patient 10. The drainage system 50 is illustrated as including a catheter 52 that is inserted into the lumbar spinal canal to the intrathecal space that contains cerebrospinal fluid. But it is also contemplated that the drainage system 50 can be used in other applications where the slow and controlled drainage of a fluid from a patient is desired.

The drainage system 50 includes the catheter 52 that provides drainage access to a source of fluid to be drained, a drain line 54 connected to the catheter 52, a collection reservoir 80, a controller 90 and a valve assembly 100. In CSF-drainage applications, the catheter 52 is inserted into the lumbar spinal canal of the patient 10 to access the site requiring CSF drainage. One end of the drain line 54 is connected to the catheter 52 and an opposite end of the drain line 54 is connected to an inlet 182 (FIG. 2) of the valve assembly 100. It is contemplated that the drain line 54 and the valve assembly 100 may utilize a quick connection that allows an operator to quickly and easily attach/detach the drain line 54 to/from the valve assembly 100.

An outlet 184 (FIG. 2) of the valve assembly 100 is connected to the reservoir 80 via a second line 56. It is contemplated that the second line 56 can include a quick connection at one or both ends to allow the reservoir 80 to be quickly and easily attached/detached to/from the valve assembly 100 and/or the reservoir 80. The reservoir 80 includes an internal cavity 80a for collecting/storing the CSF drained from the patient 10. The internal cavity 80a may be sized to hold a predetermined amount of CSF (and may also be graduated) to limit and/or measure the amount of CSF drained from the patient 10.

Figure 1A:
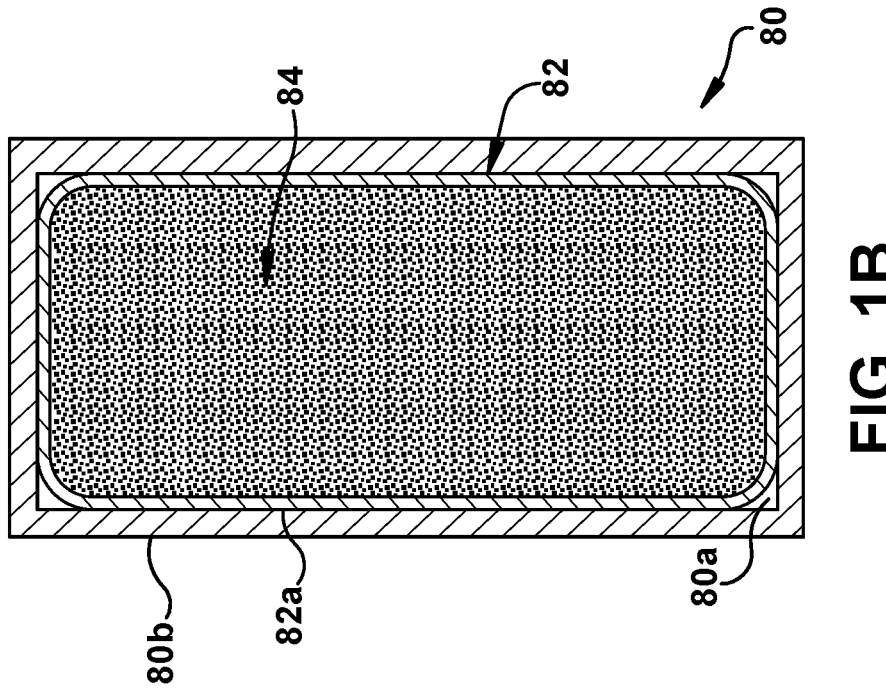
FIG. 1A is a plan view showing a cross-section of a reservoir of the drainage system of FIG. 1 taken along line 1-1 of FIG. 1 and showing an expandable pouch or bag of the reservoir in a first, collapsed condition.
Figure 1B:
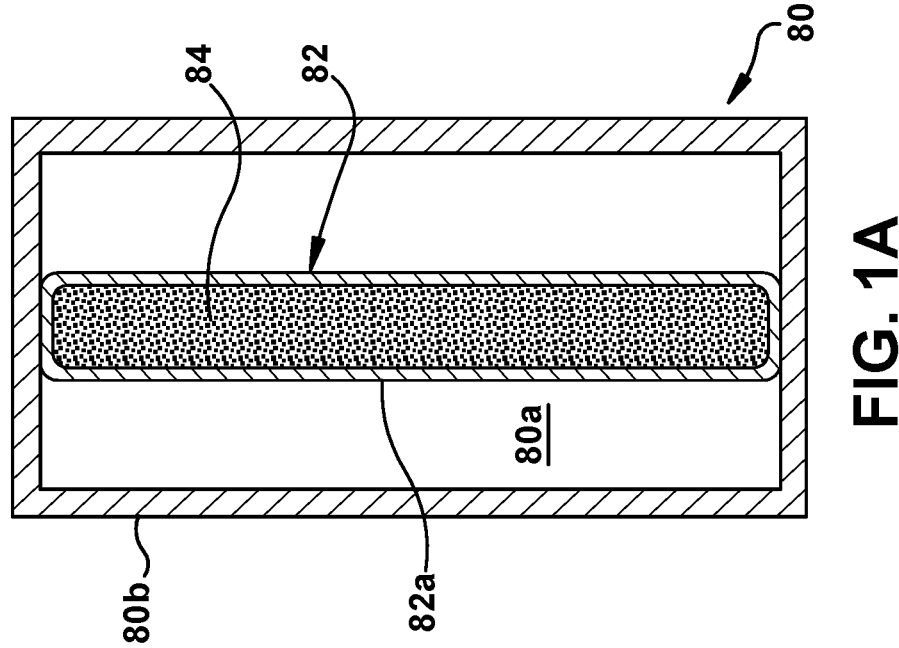
FIG. 1B is a cross-sectional view as in FIG. 1A, but with the pouch/bag in a second, expanded condition.

A collapsible/expandable pouch or bag 82 may be disposed in the internal cavity 80a. In this embodiment, fluid collected within the reservoir 80 is accumulated within the expandable pouch/bag 82, which can expand to fill the internal cavity 80a, which thus fixes a maximum volume of fluid that can be collected. The expandable pouch/bag 82 typically would be supplied in a collapsed state (shown schematically in FIG. 1A) and be adapted to expand in order to accommodate fluid (e.g. CSF) that is collected. An expandable member 84, e.g., a sponge, may be placed within the expandable bag 82 and a vacuum applied to the bag 82 in order to compress the bag 82 against the expandable member 84 to achieve the as-supplied collapsed state of the bag 82; i.e. such that in the collapsed state as-supplied, the bag 82 is under vacuum (FIG. 1A). The vacuum will cause walls 82a of the bag 82 to collapse and compress the expandable member 84, against its expansion bias which otherwise would tend to expand the bag 82. Once connected to the valve assembly 100, the expansion bias of the expandable member 84 presses on the walls 82a to expand the bag 82, which may generate a corresponding suction pressure on the drain line 54 via the second line 56 and the valve assembly 100. This suction pressure can serve as a driving force to promote drainage of the CSF from the patient 10 in a manner that does not rely on hydrostatic pressure; i.e. a Bernoulli balance with the patient's head located above the reservoir 80. The expandable bag 82 continues to sustain a mild suction that provides a driving force for CSF drainage as long as the expandable member 84 therein continues to bias the bag 82 to further expand its volume. As the CSF fills the internal cavity, the expandable member 84 expands to maintain the suction pressure on the drain line 54 by continuing to bias the bag 82 to further expand. But once the expandable bag 82 has reached its maximum volume (i.e. once it has expanded to fill the internal cavity 80a—shown in FIG. 1B), no amount of additional bias will cause it to further expand, and the mild vacuum driving force for CSF drainage will be removed. In this manner, once the reservoir 80 has been filled to its maximum volume, no further CSF will be drained.

Figures 2, 3:
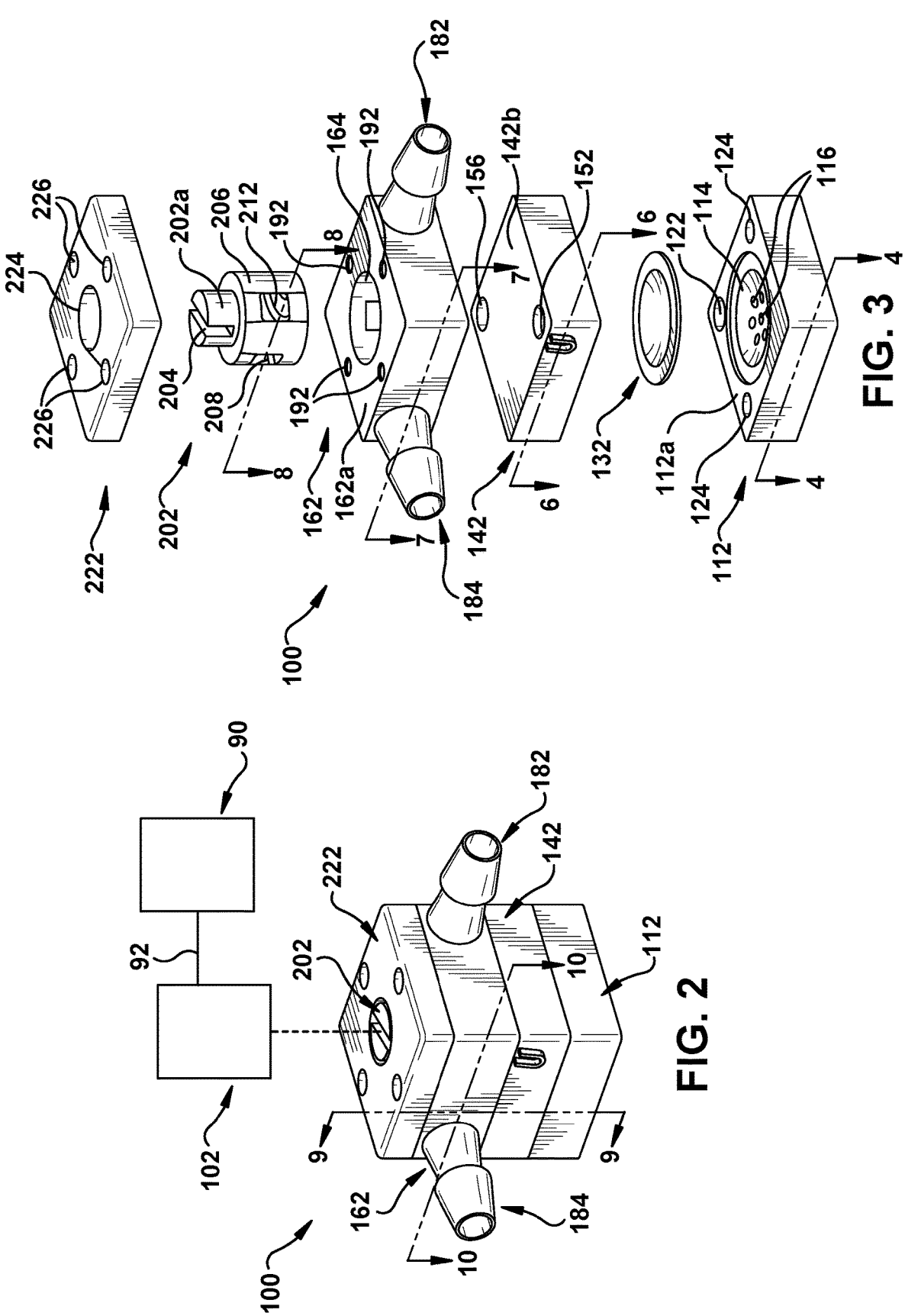
FIG. 2 shows a perspective view of a valve assembly of the drainage system of FIG. 1.
FIG. 3 is an exploded view of the valve assembly shown in FIG. 2.

Referring to FIG. 2, a motor 102 is attached to the valve assembly 100 for rotating a valve plug 202 of the valve assembly 100. The motor 102 is illustrated schematically in FIG. 2 and may be a stepper motor with a shaft for engaging the plug 202 in the valve assembly 100. The motor 102 may be configured to turn the plug 202 in one direction or to oscillate the plug 202, as described in detail below.

The controller 90 is connected to the motor 102 to control the actuation of the motor 102. The controller 90 may be a conventional microprocessor that is programmed to control the actuation of the motor 102 according to a desired cycle. Referring to FIG. 1, the controller 90 is illustrated as being attached to the reservoir 80; e.g. as part of a common assembly. A control line 92 extends from the controller 90 to the motor 102 to control the operation of the same. It is contemplated that the motor 102 may be controlled using wired or wireless connection methods. The controller 90 may include a power source (not shown), e.g., a battery for allowing the controller 90 to supply power to the motor 102. Alternatively, the motor 102 can include a power source (not shown) and the controller 90 can be programmed to determine when power from the power source is supplied to the motor 102.

Referring to FIGS. 2 and 3, the valve assembly 100 is shown in detail. In the illustrated embodiment the valve assembly 100 is provided as a series of stacked elements, each being formed (e.g. molded, machined or 3D-printed) with interior features to provide appropriate ducting and flow passages as hereafter described when the respective elements are stacked. In this embodiment the stacked elements include a lower chamber body 112, an upper chamber body 142, a valve body 162, and a cap 222. The remainder of the description is provided with respect to the aforementioned stacked-element structure. However, it is contemplated that the valve assembly 100 may be constructed in a different manner—e.g. the entire assembly 100 may be made via additive manufacturing as a single piece.

Figures 8, 9:
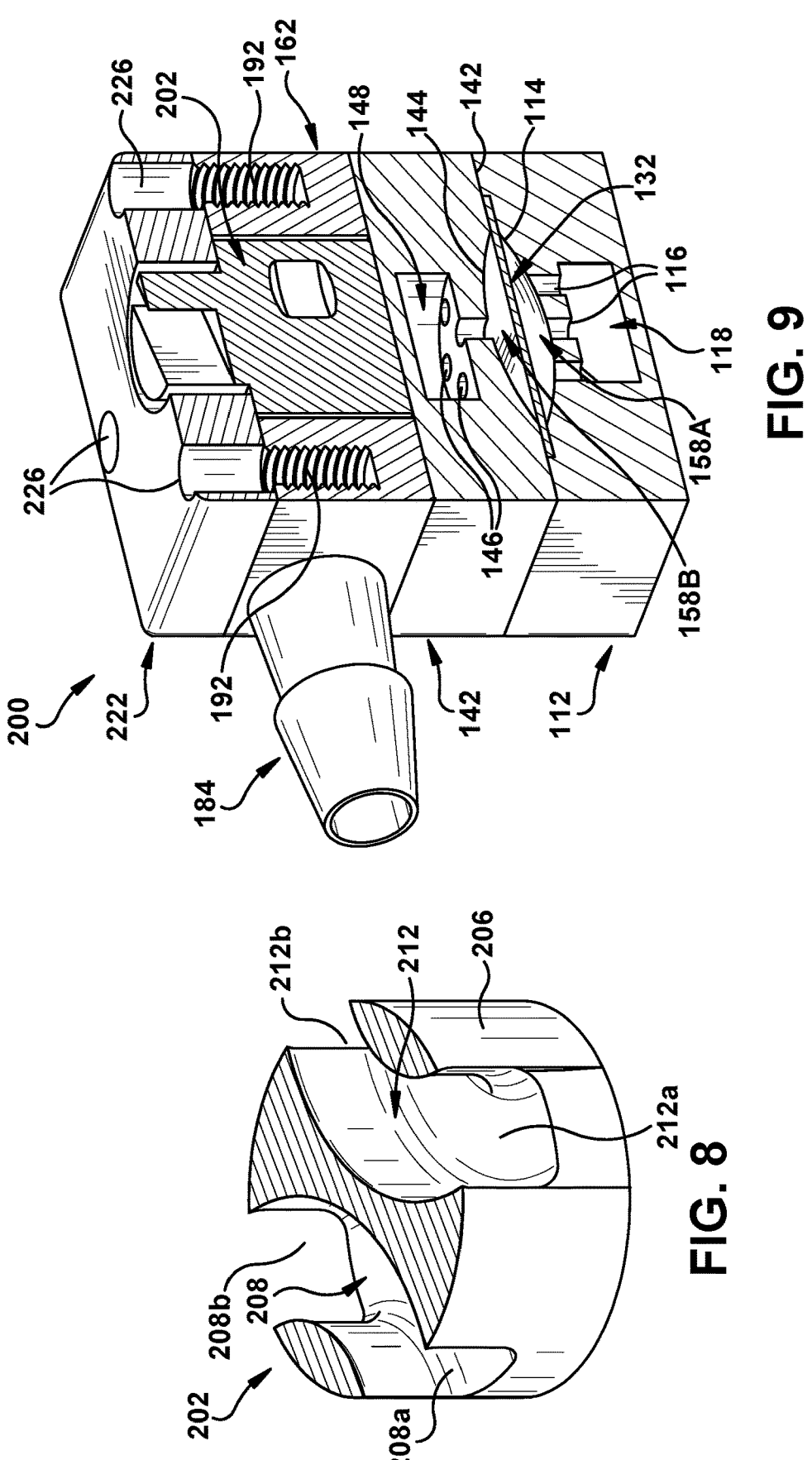
FIG. 8 is a perspective view showing a cross-section of a valve plug of the valve assembly of FIG. 2 taken along line 8-8 of FIG. 2.
FIG. 9 is a perspective view showing a cross-section of the valve assembly of FIG. 1 taken along line 9-9 of FIG. 2.

The lower chamber body 112 and upper chamber body 142 together define a diaphragm chamber to accommodate a diaphragm 132 as will be further described. The diaphragm chamber is defined by a first dome-shaped recess 114 formed in an upper surface 112a of the lower chamber body 112 (FIG. 3), and a second dome-shaped recess 144 formed in a lower surface 142a of the upper chamber body 142 (FIG. 9). A plurality of holes 116 extend through the recess 114 to provide communication with a lower passage 118 (FIG. 4) of the lower chamber body 112.

Figure 4:
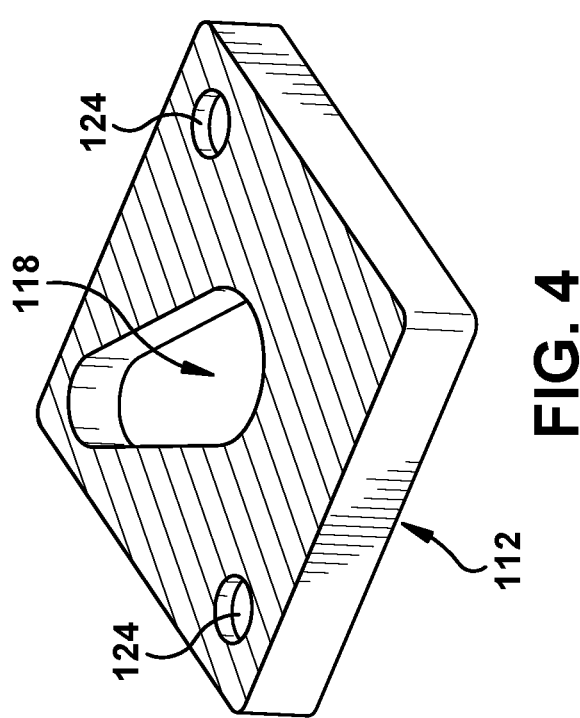
FIG. 4 is a perspective view showing a cross-section of a lower chamber body of the valve assembly of FIG. 2 taken along line 4-4 of FIG. 3.

Referring to FIG. 4, the lower passage 118 is oblong-in-shape and extends from the plurality of holes 116 (FIG. 3) to a lower passage outlet 122 (FIG. 3) at one corner of the lower chamber body 112. The lower passage outlet 122 (FIG. 3) extends from the lower passage 118 to the upper surface 112a of the lower chamber body 112. Together, the lower passage outlet 122 (FIG. 3), the lower passage 118 and the plurality of holes 116 define a lower conduit through the lower chamber body 112.

Holes 124 extend through opposite corners of the lower chamber body 112 for securing the lower chamber body 112 to the upper chamber body 142, as described in detail below.

The lower chamber body 112 is illustrated as a single unitary body with the lower chamber body 112 disposed therein. It is contemplated that the lower chamber body 112 can be manufactured using a conventional additive manufacturing method, also referred to as 3D printing. It is also contemplated that the lower chamber body 112 can be manufactured from two or more separate bodies that are joined together to define the various features of the lower chamber body 112 described in detail above. The separate bodies can be joined together using conventional fasteners, adhesives, etc. so long as when the separate bodies are joined together the various passages in the lower chamber body 112 are fluid tight.

Figure 5:
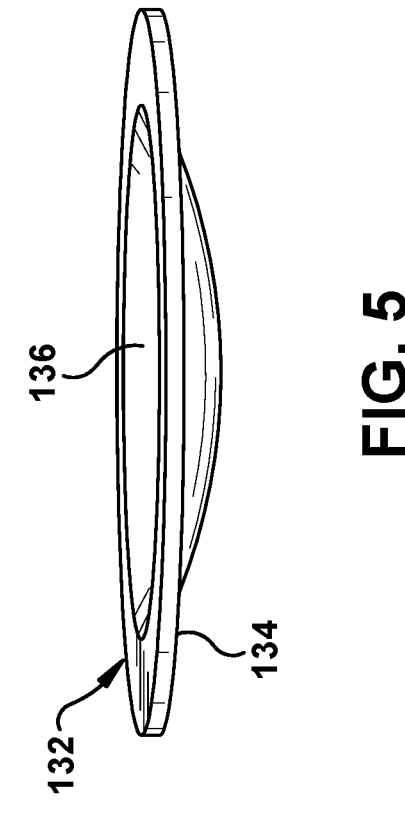
FIG. 5 is a perspective view of a diaphragm of the valve assembly of FIG. 2.

The diaphragm 132 is disposed between the lower chamber body 112 and the upper chamber body 142. Referring to FIG. 5, the diaphragm 132 has a central dome-shaped portion 136 that is contoured as described in detail below. An outer peripheral rim 134 extends about the dome-shaped portion 136. The diaphragm 132 is made from a flexible material that is selected to allow the dome-shaped portion 136 to flex, e.g. so that it can be concave upward such that it abuts conformally against the first dome-shaped recess 114, or concave downward so that it abuts conformally against the second dome-shaped recess 144, as described in detail below.

Figures 6, 7:
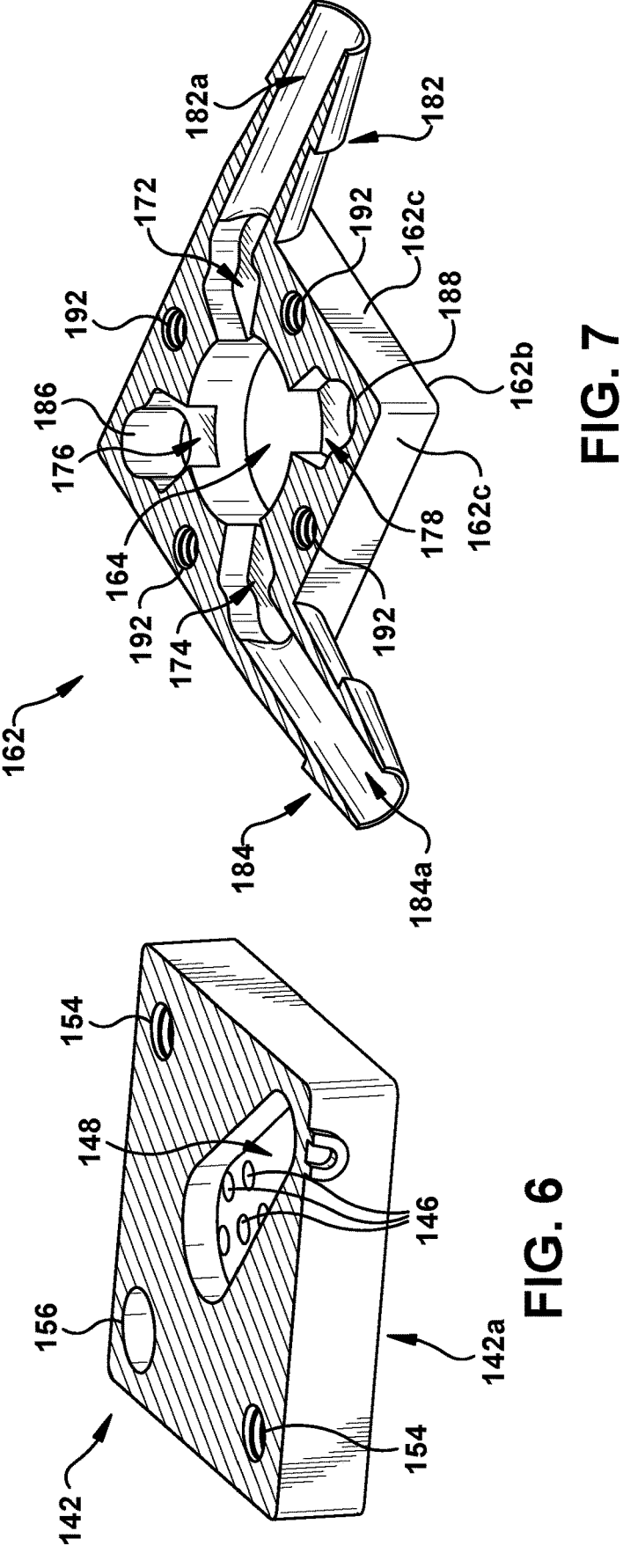
FIG. 6 is a perspective view showing a cross-section of an upper chamber body of the valve assembly of FIG. 2 taken along line 6-6 of FIG. 3.
FIG. 7 is a perspective view showing a cross-section of a valve body of the valve assembly of FIG. 2 taken along line 7-7 of FIG. 3.

Referring to FIG. 3, the upper chamber body 142 is attached to the lower chamber body 112 to capture the diaphragm 132 therebetween within the diaphragm chamber defined between the respective first (lower) and second (upper) dome-shaped recesses 114 and 144. Referring to FIG. 6, a plurality of holes 146 extend within the upper chamber body 142 to provide communication between the second recess 144 (FIG. 9) and an upper passage 148 of the upper chamber body 142. The upper passage 148 is oblong-in-shape and extends from the plurality of holes 146 to an upper passage outlet 152 (FIG. 3) at one corner of the upper chamber body 142. The upper passage outlet 152 (FIG. 3) extends from the upper passage 148 through an upper surface 142b of the upper chamber body 142. Together, the upper passage outlet 152 (FIG. 3), the upper passage 148 and the plurality of holes 146 define an upper conduit through the upper chamber body 142.

Threaded mounting holes 154 extend into the upper chamber body 142 adjacent to opposing corners thereof. The threaded mounted holes 154 are dimensioned and positioned to align with holes 124 in the lower chamber body 112. The holes 124 are dimensioned to receive fasteners, e.g., screws that thread into the threaded mounting holes 154 to secure the lower chamber body 112 to the upper chamber body 142. It is contemplated that a gasket or a similar sealing member (not shown) may be disposed between the upper surface 112a of the lower chamber body 112 and the lower surface 142a of the upper chamber body 142 to promote or reinforce a fluid-tight seal between the respective bodies 112, 142.

The upper chamber body 142 is illustrated as a single unitary body with the upper passage 148 disposed therein. It is contemplated that the upper chamber body 142 can be manufactured using a conventional additive manufacturing method, also referred to as 3D printing. It is also contemplated that the upper chamber body 142 can be manufactured from two or more separate bodies that are joined together to define the various features of the upper chamber body 142 described in detail above. The separate bodies can be joined together using conventional fasteners, adhesives, etc. so long as when the separate bodies are joined together the various passages in the upper chamber body 142 are fluid tight.

A through hole 156 extends through one corner of the upper chamber body 142 between the lower surface 142a and the upper surface 142b. The through hole 156 is dimensioned and positioned to align with the lower passage outlet 122 (FIG. 3) in the lower chamber body 112, as described in detail below.

Referring to FIG. 9, the first recess 114 of the lower chamber body 112 and the opposing second recess 144 of the upper chamber body 142 define the diaphragm chamber of the valve assembly 100. The first recess 114 defines a first wall of the diaphragm chamber and the second recess 144
defines a second wall of the diaphragm chamber. The
diaphragm 132 is captured within the diaphragm chamber to
divide it into a first chamber cavity 158A and a second
chamber cavity 158B. The first chamber cavity 158A is
defined between a lower surface of the diaphragm 132 and
the surface of the recess 114. The second chamber cavity
158B is defined between the upper surface of the diaphragm
132 and the surface of the recess 144. Because the recesses
114, 144 are fixed, movement of the diaphragm 132 in the
inner cavity changes the volume of the first chamber cavity
158A and the second chamber cavity 158B, but the overall
volume of the diaphragm chamber remains constant.

Referring to FIGS. 2 and 3, when assembled the valve
body 162 abuts (e.g. is attached to) the upper surface 142b
of the upper chamber body 142. The valve body 162
includes a central opening 164 that extends through the
valve body 162 from an upper surface 162a to a lower
surface 162b thereof. The central opening 164 is cylindrical-
in-shape and is dimensioned to allow the valve plug 202 to
rotate freely therein, as described in detail below.

Referring to FIG. 7, four chambers 172, 174, 176, 178 are
equally spaced about a periphery of the central opening 164
and each fluidly communicates with the central opening 164.
The first chamber 172 is fluidly connected to a bore 182a of
an inlet 182 to the valve body 162, thereby defining an inlet
passage of that body 162. The second chamber 174 is
positioned diametrically opposite (i.e. 180 degrees offset
from) the first chamber 172 in the illustrated embodiment,
and is fluidly connected to a bore 184a of an outlet 184 from
the valve body 162, thus defining an outlet passage of that
body 162. The inlet 182 and the outlet 184 are both illus-
trated as barbed fittings that extend from respective side
walls 162c of the valve body 162. It is also contemplated that
the inlet 182 and outlet 184 may be or comprise other
conventional fittings that find particular application in mak-
ing fluid-tight connections.

The third chamber 176 is circumferentially equidistant
from the first chamber 172 and the second chamber 174
relative to the central opening 164 in the illustrated embodi-
ment. A hole 186 extends through the lower surface 162b of
the valve body 162 and is positioned to establish fluid
communication with the third chamber 176. The hole 186 is
positioned as described in detail below. The fourth chamber
178 positioned diametrically opposite the third chamber
176, circumferentially equidistant from the first chamber
172 and the second chamber 174. A hole 188 extends
through the lower surface 162b of the valve body 162 and is
positioned to establish fluid communication with the fourth
chamber 178. The hole 188 is positioned as described in
detail below.

Four blind threaded mounting holes 192 extend into the
valve body 162 from the upper surface 162a (FIG. 3). The
four threaded mounting holes 192 are equally spaced about
the periphery of the central opening 164 and positioned as
described in detail below.

The lower surface 162b of the valve body 162 is posi-
tioned in registry with the upper surface 142b of the upper
chamber body 142. The hole 186 is positioned and dimen-
sioned to align with the through hole 156 (FIG. 3) in the
upper chamber body 142 to establish fluid communication
therewith. The hole 188 is positioned and dimensioned to
align with the upper passage outlet 152 to establish fluid
communication therewith.

Referring to FIG. 3, the plug 202 is dimensioned to rotate
within the central opening 164 of the valve body 162. The
plug 202 includes a driving portion 202a and a plug body

206. The driving portion 202a includes a slot or groove 204
that is keyed to engage with a drive shaft of the motor 102.
It is also contemplated that the plug 202 may be integrated
with or as part of a drive shaft for the motor 102.

Referring to FIG. 8, the plug body 206 includes a first
passage 208 and a second passage 212. The passages 208,
212 are arcuate in shape and each includes a first end 208a,
212a and a second end 208b, 212b. The first passage 208 and
the second passage 212 are positioned and configured such
that as the plug 202 rotates within the valve body 162 the
passages 208, 212 alternately establish particular lines of
fluid communication between various ones of the chambers
172, 174, 176, 178, as described in detail below.

Referring back to FIG. 3, as assembled the cap 222 abuts
(e.g. is attached to) the upper surface 162a of the valve body
162. The cap 222 includes a central opening 224 and four
spaced-apart through holes 226. The cap 222 is configured
to secure the plug 202 in the central opening 164 of the valve
body 162 when assembled. The central opening 224 is
dimensioned and positioned to accommodate the driving
portion 202a of the plug 202 so that it is accessible by the
drive shaft of the motor 102. The holes 226 are dimensioned
and positioned to align with the thread mounting holes 192
in the valve body 162 (see, FIG. 9). A fastener (not shown)
is dimensioned to extend through each hole 226 and thread
into the threaded mounting holes 192 to secure the cap 222
to the valve body 162.

The valve assembly 100 will now be described in relation
to a mode of operation. Referring to FIG. 1, the inlet 182 is
attached to the drain line 54, which in turn is connected to
the catheter 52. The outlet 184 is attached to the second line
56, which in turn is connected to the reservoir 80. As noted
above, the bag/pouch 82 is configured to have a slight
vacuum such that upon connection with the valve assembly
100 a predetermined suction is applied to the outlet 184 of
the valve assembly 100.

Figures 10, 11:
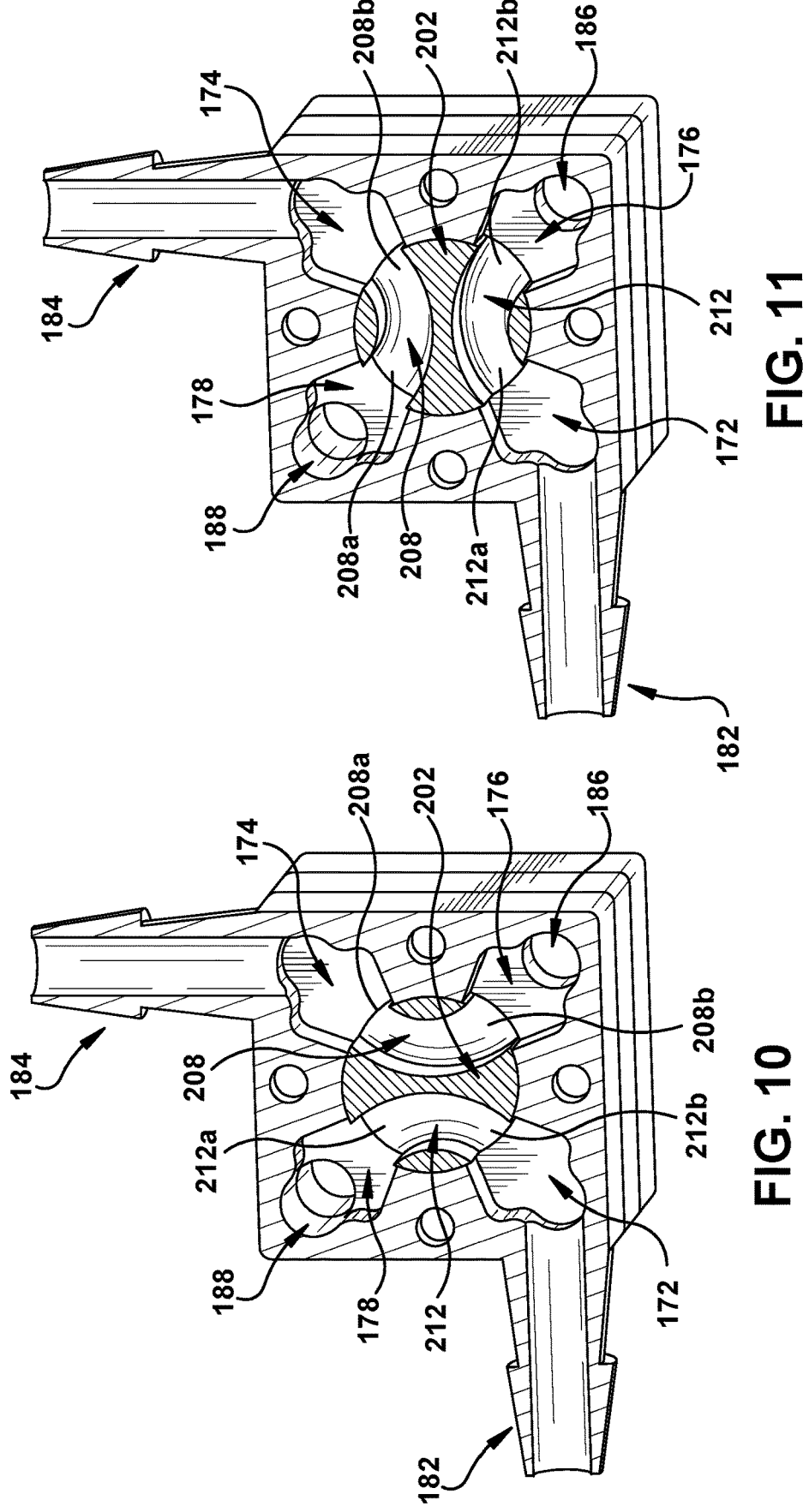
FIG. 10 is a cross-sectional view of the valve assembly of FIG. 2 taken along line 10-10 of FIG. 2 and showing the valve plug in a first valve position.
FIG. 11 is a cross-sectional view as in FIG. 10, but with the valve plug in a second valve position.

Referring to FIG. 10, the operation of the valve assembly
100 will be described with the plug 202 starting in a first
actuation state. In the first actuation state, the first passage
208 in the plug 202 provides fluid communication between
the second chamber 174 and the third chamber 176 of the
valve body 162, and by extension between the outlet 184 and
the hole 186. The hole 186 extends through the valve body
162 and fluidly communicates with the through hole 156
(FIG. 3), the lower passage outlet 122 (FIG. 3), the lower
passage 118 (FIG. 4), the plurality of holes 116 (FIG. 3) and
the first chamber cavity 158A. As will thus be appreciated,
the third chamber 176, the hole 186, the through hole 156,
the lower passage outlet 122, the lower passage 118 and the
plurality of holes 116 (FIG. 3) define a first chamber passage
to the first chamber cavity 158A. It will be seen that when
the valve plug 202 is in the first actuation state ultimately the
outlet 184 of the valve body 162 is placed in fluid commu-
nication with the first chamber cavity 158A of the diaphragm
chamber via the outlet passage (constituted by second cham-
ber 174) and the first chamber passage as defined in the
preceding sentence.

Also in this first actuation state (FIG. 10) the second
passage 212 of the rotor plug 202 provides fluid communi-
cation between the first chamber 172 and the fourth chamber
178, and by extension between the inlet 182 and the hole
188. The hole 188 (FIG. 7) extends through the valve body
162 and fluidly communicates with the upper passage outlet
152 (FIG. 3), the upper passage 148 (FIG. 6), the plurality
of holes 146 (FIG. 6) and the second chamber cavity 158B.
As will thus be appreciated, the hole 188, the upper passage
outlet 152, the upper passage 148 and the plurality of holes 146 define a second chamber passage. Accordingly, when the valve plug 202 is in the first actuation state ultimately the inlet 182 of the valve body is placed in fluid communication with the second chamber cavity 158B of the diaphragm chamber via the inlet passage (constituted by first chamber 172) and the second chamber passage as defined in the preceding sentence.

Referring to FIG. 9, when the plug 202 is in the first actuation state as described above the predetermined suction in the reservoir 80 (e.g. resulting from the expansive bias of the expandable member 84 within the bag/pouch 82) is drawn against the first chamber cavity 158A. This vacuum will tend to draw the diaphragm 132 toward the first dome-shaped recess 114 until ultimately it becomes seated against that recess 114. The resulting suction is configured to be sufficient such that the first chamber cavity 158A contracts as the second chamber cavity 158B expands due to the downward deflection of the diaphragm 132, the resulting suction pressure applied via holes 146 to the upper passage 148 will draw CSF from the catheter 52. More simply, when the valve plug 202 is in the first actuation state, suction pressure applied beginning from or at the reservoir 80 ultimately leads to drawing CSF from the patient 10 and into the second chamber cavity 158B. The drawing of fluid into the second chamber cavity 158B can continue under the influence of this pressure (suction) gradient until the second chamber cavity 158B has become fully expanded; i.e. until the diaphragm (i.e. the dome-shaped portion thereof) has become seated conformally against the first (lower) recess 114 in the lower chamber body 112. At that point, because the second chamber cavity 158B can expand no further it can accommodate no more fluid, and flow will cease.

It is also contemplated that upon connection of the drainage system 50 to the patient 10 the pressure of the CSF in the patient 10 may supply sufficient driving force to initiate drainage into the second chamber cavity 158B (in the first actuation state of the plug 202) without application of suction at or from the reservoir 80. In this circumstance, the head pressure of the CSF is sufficient to drive flow and to deflect the diaphragm 132 toward the lower recess 114 ultimately into conformal contact therewith.

After a predetermined amount of time, the controller 90 can actuate the motor 102 to rotate the valve plug 202 (e.g. 90° in the illustrated embodiment) to a second actuation state, illustrated in FIG. 11. In the second actuation state, the first passage 208 of the valve plug 202 establishes fluid communication between the fourth chamber 178 and the second chamber 174 (i.e. the outlet passage), and by extension between the hole 188 and the outlet 184. As noted above, the hole 188, the upper passage outlet 152 (FIG. 3), the upper passage 148 (FIG. 6) and the plurality of holes 146 (FIG. 6) define the second chamber passage to the second chamber cavity 158B. In this respect, fluid communication is established between the reservoir 80 and the second chamber cavity 158B of the diaphragm chamber via the outlet passage and the second chamber passage.

Also, in this second actuation state the second passage 212 of the valve plug 202 establishes fluid communication between the first chamber 172 (i.e. the inlet passage) and the third chamber 176, and by extension between the inlet 182 of the valve body and the hole 186. As noted above, the hole 186, the through hole 156 (FIG. 3), the lower passage outlet 122 (FIG. 3), the lower passage 118 (FIG. 4) and the plurality of holes 116 (FIG. 3) define the first chamber passage to the first chamber cavity 158A. In this respect, fluid communication is established between the catheter 52 (connected via drain line 54 to the inlet 182) and the first chamber cavity 158A of the diaphragm chamber via the inlet passage and the first chamber passage.

When the plug 202 reaches the second actuation state, the suction drawn from the reservoir 80 and/or the head pressure supplied at the source of CSF in the patient 10 causes the diaphragm 132 to deflect toward the second dome-shaped recess 144 of the upper chamber body 142; i.e. in the opposite direction compared to when the plug 202 is in the first position. As the diaphragm 132 moves, CSF from the patient 10 is now drawn into the first chamber cavity 158A and CSF fluid resident in the second chamber cavity 158B (i.e. CSF that was filled therein when the plug 202 was in the first actuation state) is forced out the outlet 184 and flows to the reservoir 80 where it is collected within the bag/pouch 82.

After a predetermined amount of time, the controller 90 again can actuate the motor 102 to rotate the valve plug 202 (e.g. 90°) to return it to the first actuation state, illustrated in FIG. 10. Once the valve plug 202 is back in the first actuation state, the first chamber cavity 158A is once again is fluidly connected to the reservoir 80 (via outlet 184) and the second chamber cavity 158B is fluidly connected to the catheter 52 (via inlet 182). The head pressure of the CSF in the patient 10 and/or the suction pressure from the reservoir 80 causes the diaphragm 132 to deflect towards the recess 114 in the lower chamber body 112. As the diaphragm 132 moves, the CSF in the first chamber cavity 158A flows to the reservoir 80 while CSF from the catheter 52 is drawn into the second chamber cavity 158B. The diaphragm 132 continues to move until it reaches conformity with the lower recess 114 as previously described.

The controller 90 can be programmed to successively actuate the motor 102 to thereby oscillate the plug 202 between the first actuation state (FIG. 10) and the second actuation state (FIG. 11) for a predetermined period of time and/or according to a predetermined duty cycle; i.e. a fixed number of such oscillations per hour or per day. This oscillation causes the second chamber cavity 158B and the first chamber cavity 158A to alternately fill with CSF from the patient 10 and to alternately discharge the collected CSF within the respective chambers 158A, 158B to the reservoir 80. In particular, as the second chamber cavity 158B fills with CSF from the patient 10, the first chamber cavity 158A discharges CSF to the reservoir 80. Similarly, as the second chamber cavity 158B discharges CSF to the reservoir 80, the first chamber cavity 158A fills with CSF from the patient 10.

The alternate filling of the second chamber cavity 158B and the first chamber cavity 158A with CSF is repeated until a desired amount of CSF is drained from the patient 10, or at a rate that achieves a desired rate of drainage; e.g. in mL per hour or per day. The timing of the oscillation of the plug 202 is selected to control the rate that CSF is drained from the patient. For example, the first chamber cavity 158A and the second chamber cavity 158B may be sized to be about 1 mL (i.e. 1 cc) and the valve plug 202 may be actuated ten times per hour for ten hours to yield a total of 100 mL of CSF drained to the reservoir 80 at a rate of 10 mL per hour. If higher or lower rates are needed, the motor 102 is actuated faster or slower or the recess 114, 144 are sized to be larger or smaller.

The plug 202 may oscillate back-and-forth between the first actuation state (FIG. 10) and the second actuation state (FIG. 11); i.e. such that it rotates clockwise to one position and then counter-clockwise to the other, successively. In this operational mode, the first passage 208 always remains in fluid communication with the outlet 184 but alternates between the second chamber cavity 158B and the first chamber cavity 158A. The first passage 208 thereby is used only to alternately drain CSF from the second chamber cavity 158B and the first chamber cavity 158A. Similarly, the second passage 212 is always in fluid communication with the inlet 182 but alternates between the second chamber cavity 158B and the first chamber cavity 158A. The second passage 212 thereby is used only to alternately supply CSF from the patient 10 to the second chamber cavity 158B and the first chamber cavity 158A.

Alternatively, the plug 202 may be configured such that it is rotated only in one direction, e.g. clockwise, to achieve the disclosed oscillations. In this operational mode, in the first actuation state (FIG. 10) the first passage 208 first connects the outlet 184 to the first chamber cavity 158A. Rotation of the plug 202 90° clockwise then causes the first passage 208 to connect the inlet 182 to the first chamber 158A (see FIG. 11 wherein the first passage 208 would now be positioned where the second passage 212 is positioned). Further rotation of the plug 202 90° clockwise causes the first passage 208 to connect the inlet 182 to the second chamber 158B. Rotating the plug 202 90° clockwise again causes the first passage 208 to connect the outlet 184 to the second chamber 158B (FIG. 11). And further rotating the plug 202 90° clockwise again returns the plug 202 back to the first valve position (FIG. 10). The second passage 212 would be similarly indexed via successive 90° rotations of the plug 202. In other words, rotating the valve plug 202 in the clockwise direction causes the respective passages 208, 212 to alternately connect the inlet 182 and outlet 184 to the first chamber cavity 158A and the second chamber cavity 158B in the same manner described above for oscillating the plug 202 between the first actuation state (FIG. 10) and the second actuation state (FIG. 11); i.e. by successive 90°-rotations in opposite directions.

As will be appreciated, the disclosed valve assembly 100 provides a mechanism to achieve CSF drainage at a rate that can be assured not to exceed a rate of X per Y, where X is the max volume (e.g. in mL) of one of the upper and lower chambers 158B, 158A (assuming they have the same max volume), and Y is the time interval (e.g. in hours) of successive actuations of the valve plug 202 via the motor. Because the diaphragm 132 can be deflected only until a maximum degree is reached in either the first or second actuation states of the valve plug 202 (i.e. it can be deflected only until it is conformal with either the lower or upper recesses 114, 144), the maximum volume of the respective chambers 158A, 158B is fixed. Thus, by regulating the rate of oscillation of the valve plug, one can precisely control the maximum drainage rate for CSF, thus ensuring it does not drain faster than desired. Moreover, should the system lose power (e.g. if onboard batteries should be drained), then fluid drainage ultimately will cease once the chamber cavity 158A,B then-in-communication with the catheter 52 becomes full. This could have the effect of building up CSF pressure in the patient. But it avoids the potentially dangerous condition whereby CSF would continue to drain unconstrained in case of a power failure.

Moreover, application of a predetermined, fixed suction pressure from the reservoir 80 (e.g. using the expandable member 84 as above described) ensures a substantially constant and controllable driving force for drainage. By selecting a sponge (for example) having a predetermined degree of elasticity, its expansive bias can be selected to achieve the desired micro-pressure gradient to assure CSF drainage in a manner that does not rely on gravity or the relative geometric arrangement/position of the patient or between the catheter and the reservoir. It is also contemplated that the internal cavity 80a of the reservoir 80 may have a fixed volume that is under vacuum. The vacuum may be applied to the internal cavity 80a at the time of manufacture and the reservoir 80 sealed until a user connects the reservoir 80 to the valve assembly 100. This can be an important feature of ambulatory drainage because with the patient unconstrained, his/her position will change throughout the day or period of treatment in a manner that cannot be controlled; unlike in a clinical setting where gravity drainage can be used efficiently. Also, by selecting a desired maximum volume for the reservoir bag/pouch 82, the maximum amount of fluid drainage can be fixed. That is, once the bag/pouch 82 has been filled to its maximum volume, further drainage automatically will cease because that bag/pouch 82 will no longer expand to accommodate more fluid. This will eliminate both: the vacuum driving force resulting from such expansion if vacuum is relied on for drainage; and the head-pressure driving force originating in the patient once the downstream pressure increases to meet that head pressure (i.e. once further flow into the reservoir is impeded).

And finally, the valve system disclosed herein also acts as a check valve to impede backflow from the reservoir 80 into the patient 10. This can be a desirable feature in case the reservoir 80 encounters external forces that would tend to compress its volume (e.g. which may occur unpredictably because this is an ambulatory device). It also can be desirable once the reservoir 80 becomes full so that it does not exert a reverse pressure that tends to drive CSF back into the patient 10. The fixed max-volume chamber cavities 158A,B coupled with the plug 202 ensure that there never is a direct line of communication between the reservoir 80 and the catheter 52, so that backflow therebetween is impossible.

Although the aforementioned embodiments have been described with respect to draining CSF from a patient 10, it will be appreciated that those embodiments also may be utilized for controlled drainage from any other organ or space of or within the patient where metered, controlled, ambulatory drainage is desired.

The above description relates to use of the disclosed device for the drainage of CSF, or of other fluid from a store of such fluid within a patient, e.g. to treat a condition resulting from an excess buildup of such fluid. However, it is to be appreciated that the disclosed device also can be operated in a reverse manner, such that rather than draining fluid from a store of fluid within a patient, the device can be used to deliver a therapeutic agent from the reservoir, via the valve and catheter, into the patient at a desired location. To achieve such operation, one would reverse the flow of fluid compared to that described, for example by reversing the direction of the pressure gradient between the reservoir 80 and the body cavity where fluid is to be delivered. In one such mode of operation, the reservoir can be supplied with the therapeutic agent at an elevated pressure sufficient to drive fluid through the device into the patient.

In this embodiment, the reservoir 80 is a pressurized supply reservoir that holds the therapeutic agent. This pressurized supply reservoir is connected to the outlet 184 of the valve assembly 100 and the catheter 52 is connected to the inlet 182. It is contemplated that the bag 82 of the reservoir 80 may be filled with the therapeutic agent and the internal cavity 80a around the bag 82 may be filled with a pressurized fluid (e.g. using a gas or a volatile vapor as a pressurant). The pressurized fluid is provided under pressure sufficient to exceed the head pressure of the CSF (or other body-resident fluid or space) in the patient so that the therapeutic agent flows from the reservoir 80 to the patient during actuation of the valve assembly 100. The controller 90 may be programmed to actuate the valve assembly 100 at a desired frequency and for a predetermined time period to supply the therapeutic agent to the patient at the desired rate in a manner similar as described above for drainage.

Figure 12:
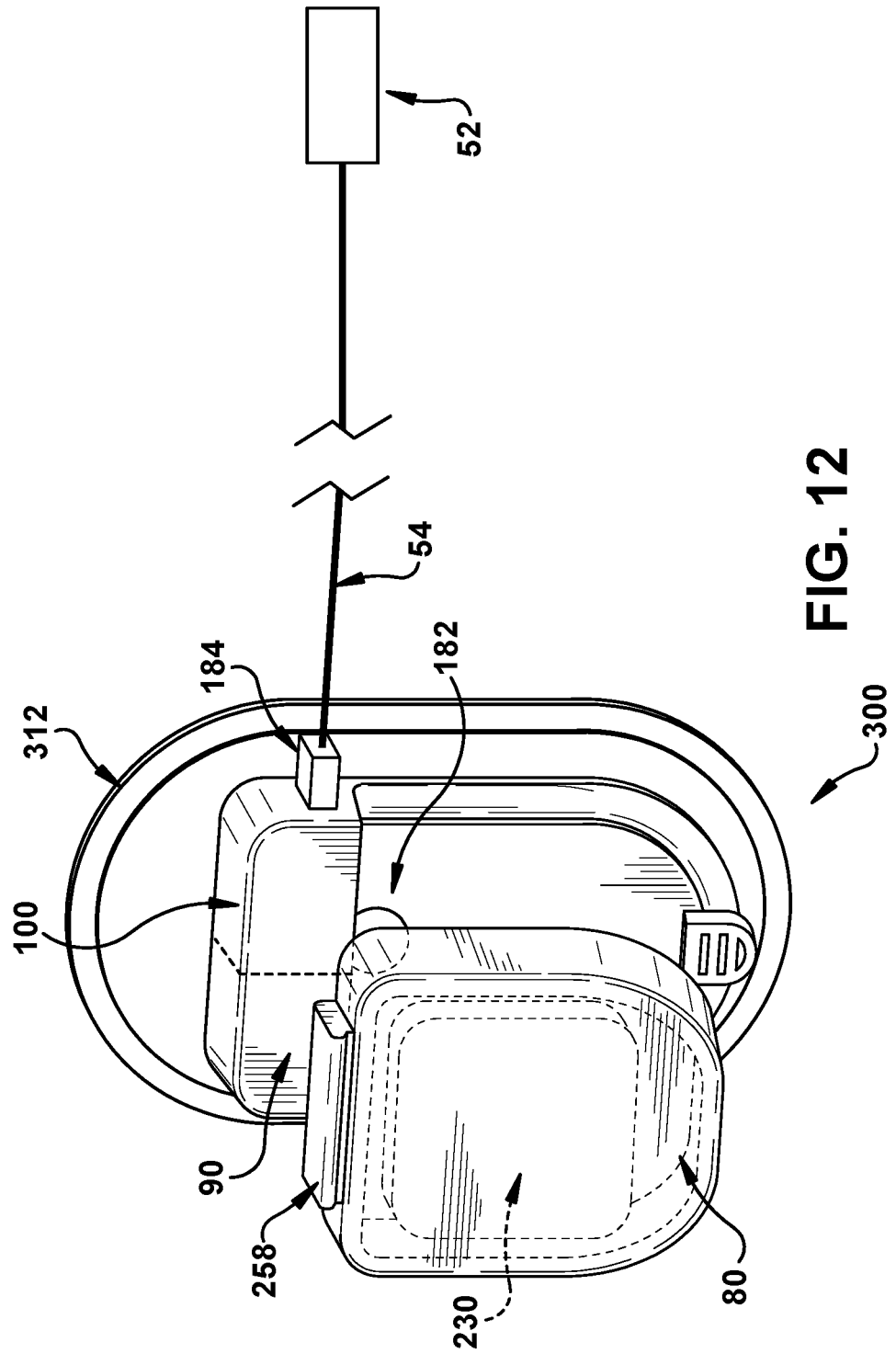
FIG. 12 is an exploded view of a pump assembly adapted to be worn by a patient, and an associated reservoir cartridge.

Referring to FIG. 12, an example embodiment is illustrated wherein the disclosed valve assembly 100 is integrated into a pump assembly 300, which constitutes a wearable unit that can be worn by an ambulatory patient undergoing CSF (or other fluid) drainage—or optionally, delivery of a therapeutic agent if operated in that manner as noted above. As shown schematically in FIG. 12, the controller 90 and valve assembly 100 are integrated into the pump assembly 300, which as illustrated can take the form of a substantially flattened-form factor device and can be worn as an adhesive patch. The reservoir 80 can be provided in a removable reservoir cartridge 250, that can be reversibly fitted and secured to the pump assembly 300 in order to place the reservoir 80 in fluid communication with the valve assembly 100 to facilitate drainage/delivery of fluid therefrom/thereto.

Figure 13B:
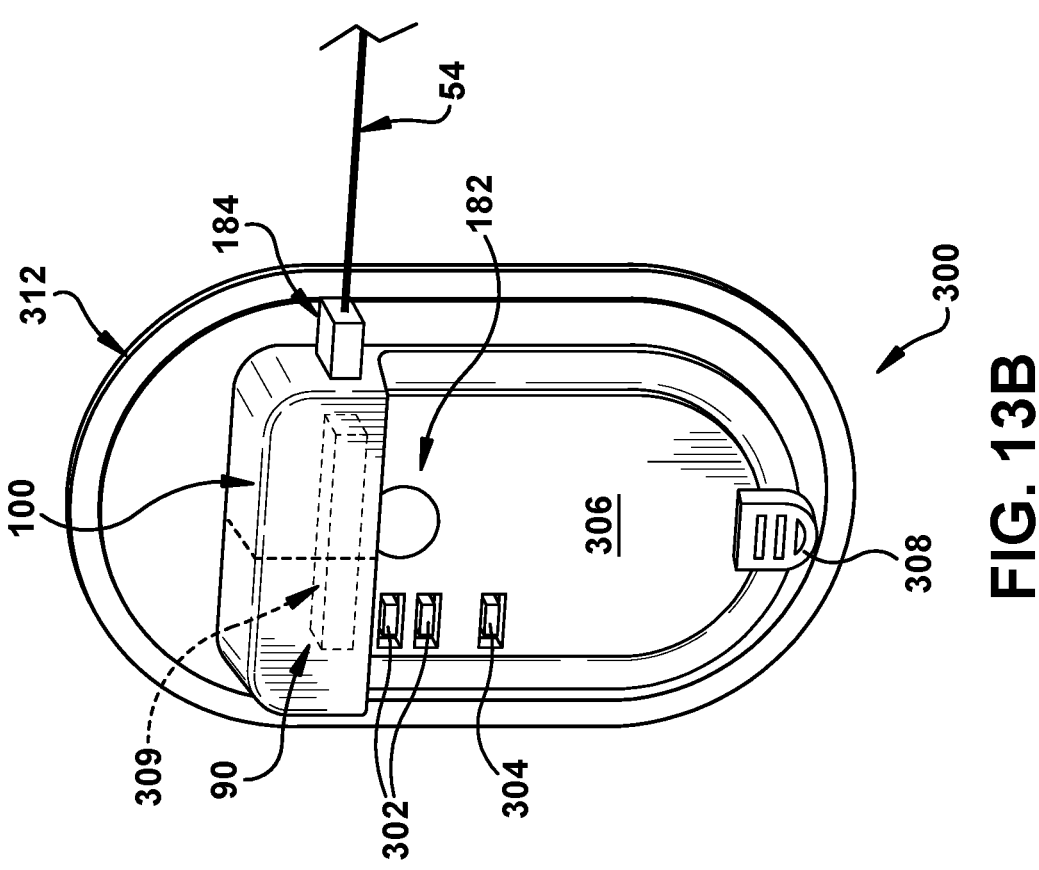
FIG. 13B is a perspective view of the pump assembly of FIG. 12.

Specifically, referring to FIG. 13B, the pump assembly 300 defines a receptacle 306 for receiving the reservoir cartridge 250. It is contemplated that the power source for supplying energy to the motor that drives the valve assembly may be a battery 230 integrated with the reservoir cartridge 250. In this manner, when the reservoir cartridge 250 is fitted to the pump assembly 300 in the receptacle 306, the battery 230 is brought into electrical communication with the motor via electrical contacts 252 positioned on the cartridge 250 engaging mating contacts 302 (FIG. 13B) positioned on the pump assembly 300. In this manner, each time the cartridge is replaced (e.g. because its reservoir 80 has become filled with drained fluid or depleted of therapeutic fluid delivered to the patient), a fresh battery is supplied to the motor to ensure reliable operation.

The reservoir cartridge 250 may also include a radio frequency identification device (RFID) 254 or other indicator, e.g. bar code, that identifies the volume of the reservoir 80. When installed to the pump assembly 300, the RFID 254 or other indicator may be read by a detector 304 (FIG. 13B) integrated with the pump assembly 300 and communicating with the onboard controller 90 so that the controller 90 will know the maximum amount of CSF (or other fluid) that can be held by the reservoir 80. The controller 90 then can be programmed to operate so as to drain only so much CSF as the reservoir 80 can hold, and then optionally to alarm (e.g. via audible or visually perceptible signal) once the maximum volume of drained CSF has been achieved. Alternatively, when operated to deliver a therapeutic agent, the RFID 234 or other indicator may indicate the volume of agent for delivery, such that the controller can regulate the rate and volume of delivery, and similarly alarm when the therapeutic agent has been depleted.

Figure 13A:
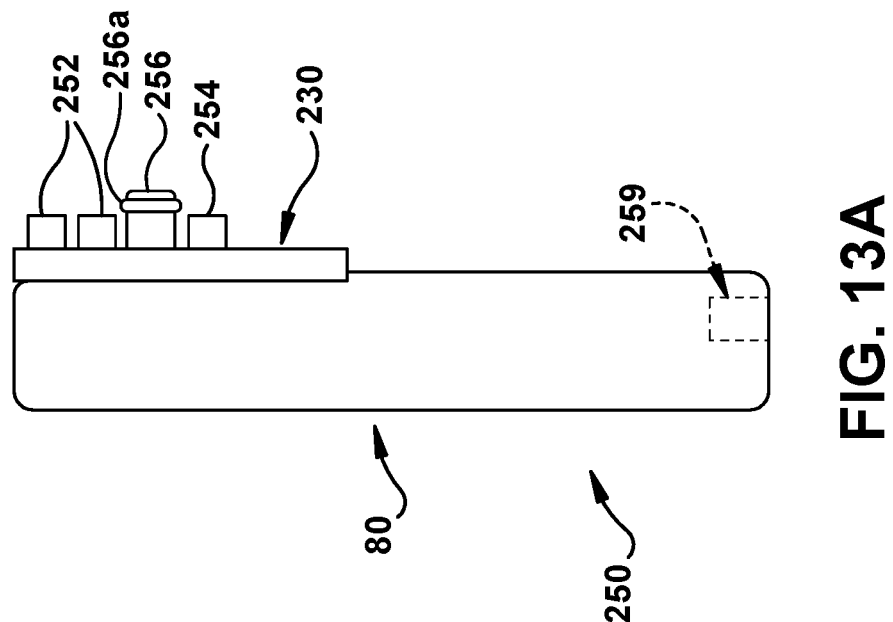
FIG. 13A is a side view of the reservoir cartridge of FIG. 12.

The receptacle 306 may include the mating contacts 302 that are positioned to engage the electrical contacts 252 of the reservoir cartridge 250 when the reservoir cartridge 250 engages the pump assembly 300. The detector 304 may be positioned in the receptacle 306 at a location that allows the detector 304 to read the RFID 254 or other indicator that is on the reservoir cartridge 250. It is contemplated that the pump assembly 300 and/or the reservoir cartridge 250 may include retaining features, e.g. interference fits, snap-fits, spring loaded tabs, etc. that may be used to secure the reservoir cartridge 250 to the receptacle 306. In the illustrated embodiment, the pump assembly 300 includes a spring-biased tab 308 at its base, which cooperates with a boss 258 extending from an upper end of the cartridge 250 and adapted to be received in a cooperating recess 309 (FIG. 13B) within the pump assembly 300. To fit the cartridge 250, first its boss 258 is fitted into the recess 309 (FIG. 13B) or similar device for securing the reservoir cartridge 250 in the receptacle 306. Then the base of the cartridge 250 is pressed against the pump assembly 300 wherein the tab 308 interferes with a flange or recess 259 (FIG. 13A) in the cartridge 250 to retain it in-place. To release the cartridge 250, the tab 308 is deflected against its bias to remove the aforementioned interference, whereupon the cartridge 250 can be removed.

The inlet 182 of the valve assembly 100 may be located in the receptacle 306 of the pump assembly 300 and positioned and dimensioned to engage a mating port 256 (e.g. a complementary fitting) on the reservoir cartridge 250 when the reservoir cartridge 250 is installed in the receptacle 306. A seal 256a, e.g. an o-ring may be on the port 256 for providing a fluid-tight connection between the port 256 and the inlet 182. The outlet 184 of the valve assembly 100 may exit from a side of the pump assembly 300 and connect to the catheter 52 via the drain line 54. In this respect, CSF from the patient 10 (FIG. 1) may pass through the valve assembly 100 and fill the reservoir 80 of the reservoir cartridge 250 in operation, similarly as already described. Notably, the inlet 182 and outlet 184 are so-named in relation to usage of the disclosed system as a drainage device, wherein fluid enters via the inlet 182 from the patient, and is eluted via the outlet 184 to the reservoir 80. However, as already explained the system can be operated in a reverse (therapeutic-agent delivery) mode, such that the inlet 182 actually will elute fluid and the outlet 184 will draw fluid. In this sense, the inlet and outlet 182 and 184 may be thought of more generally as first and second ports, each of which can be an inlet or outlet depending on the operational mode.

It is further contemplated that an adhesive panel 312 may be attached to a rear wall of the pump assembly 300 for securing the pump assembly 300 to the patient 10 (FIG. 1). The adhesive panel 312 may be coated with a skin compatible adhesive to facilitate affixation and wearing by the patient 10 (FIG. 1). It is also contemplated that suture anchors or a belt may be used to secure the pump assembly 300 on the patient 10 (FIG. 1).

In preferred embodiments, the overall size of the pump assembly 300 and the reservoir cartridge 250 together should fall within a form-factor envelope that facilitates wearing the same during outpatient ambulation. For example, the combined device may fit within a form-factor envelope having overall dimensions no greater than about 500 mm by about 200 mm by about 100 mm, preferably no greater than about 300 mm by about 100 mm by about 50 mm, more preferably no greater than about 250 mm by about 75 mm by about 30 mm and even more preferably no greater than about 100 mm by about 70 mm by about 20 mm. It also is preferred that the combination device (pump assembly 300 and cartridge 250 with its reservoir filled to capacity) will be made of materials such that its total combined weight is less than 16 ounces, preferably less than 12 ounces, more preferably less than 8 ounces, so that the patient 10 (FIG. 1) may comfortably wear the pump assembly 300 and the reservoir cartridge 250 for extended periods of time. In use over extended periods, after the patient 10 (FIG. 1) is finished with one reservoir cartridge 250 (e.g. its reservoir either filled with drained fluid or depleted of therapeutic agent, depending on operating mode), that reservoir cartridge 250 may be removed and a fresh reservoir cartridge 250 may be placed in the receptacle 306 for continued therapy.

In disclosed embodiments the valve assembly 100 includes a valve that facilitates pumping by alternately placing in in-line communication between a collection of fluid (e.g. excess of CSF within a patient) and a target for that fluid (e.g. reservoir 80) opposing diaphragm chamber cavities, wherein an external pressure gradient supplies the driving force. In this embodiment, the diaphragm-mediated valve assembly 100 (aided by the external pressure gradient) acts as a pump. The valve assembly 100 can be constituted by other types of valves suitable to facilitate pumping when motivated by an external pressure gradient as disclosed. Moreover, the valve assembly 100 can comprise or consti-tute a conventional pump that does not rely on external pressure gradients to induce flow, but rather mechanically supplies the motive force for flow. For example, conven-tional pumps such as peristaltic pumps, positive displace-ment pumps, piston pumps, centrifugal pumps, etc. could be used.

According to an alternative embodiment illustrated in FIGS. 14-20, the valve plug 202, the valve body 162 and cap 222 described above are replaced with a plunger assembly 400 that includes a plunger 410 and a passage body 420.

Figures 16, 17:
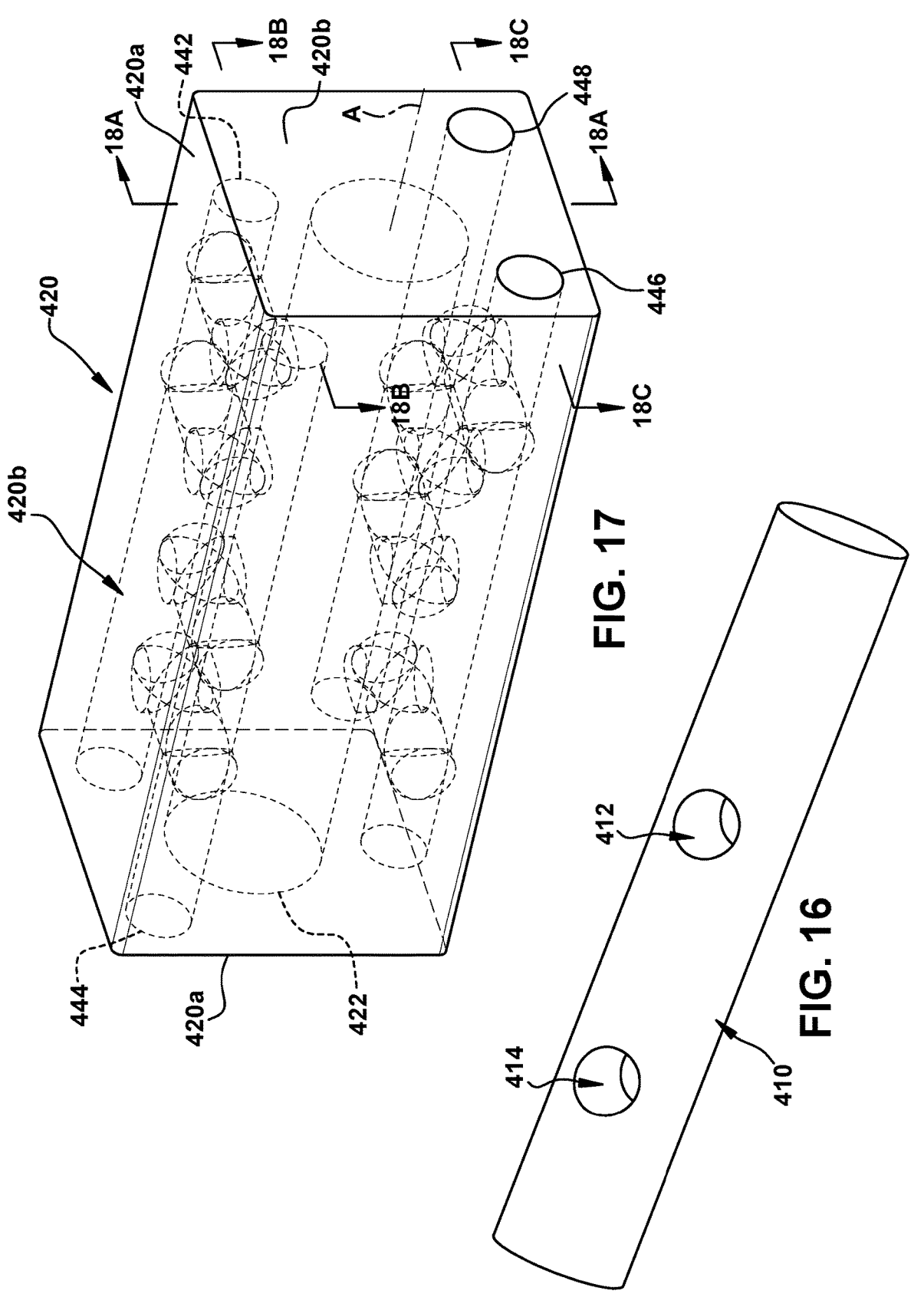
FIG. 16 is a perspective view of a plunger of the plunger assembly of FIG. 14.
FIG. 17 is a perspective view of a body of the plunger assembly of FIG. 14.

Referring to FIG. 16, the plunger 410 can be an elongated cylindrical rod having a first through hole 412 and a second through hole 414, each extending radially through the plunger 410. The first through hole 412 and the second through hole 414 are positioned and dimensioned as described in detail below.

Figures 14, 15A, 15B:
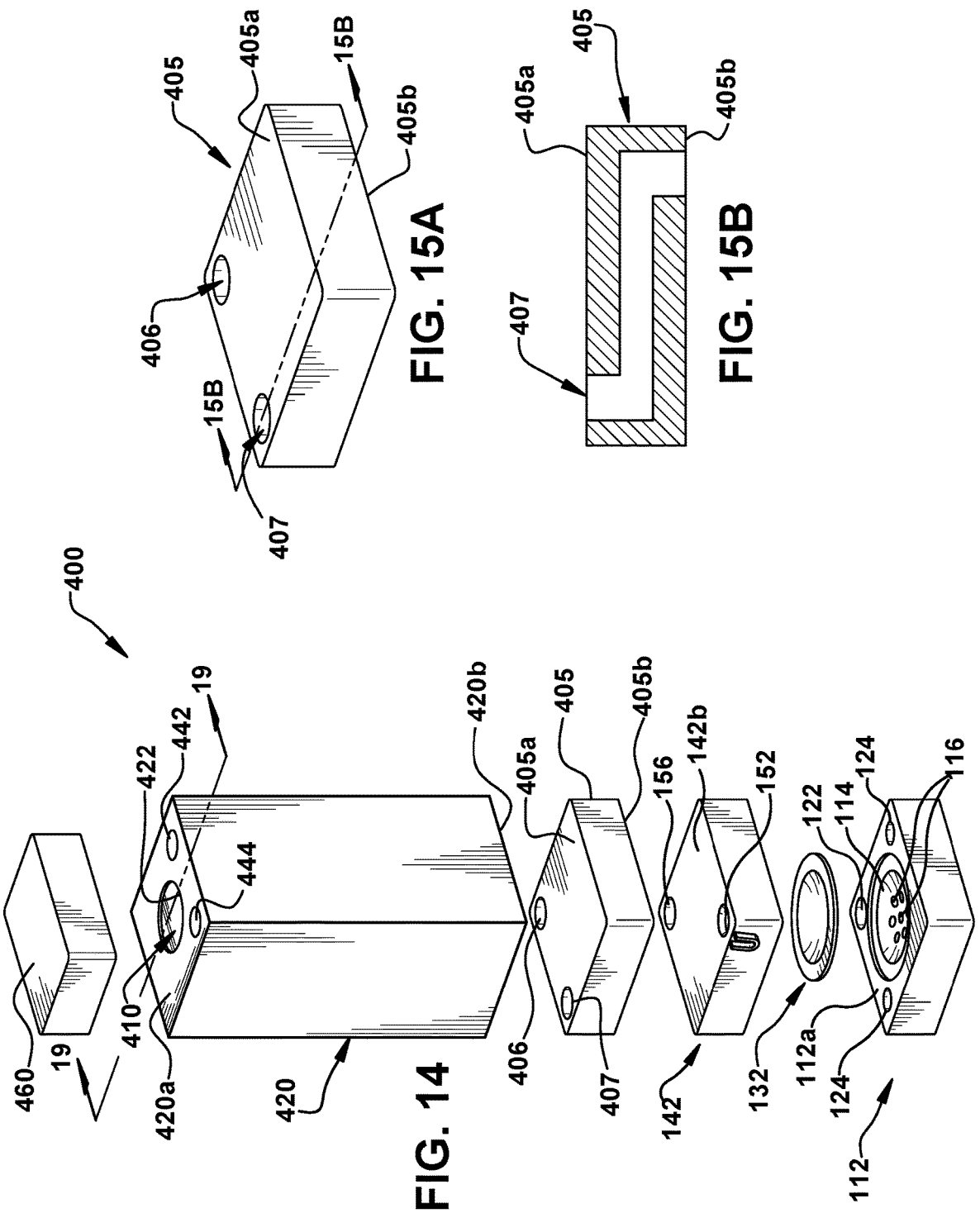
FIG. 14 is an exploded view of a plunger assembly attached to the upper chamber body and the lower chamber body of the pump assembly of FIG. 3.
FIG. 15A is a perspective view of an adapter of the plunger assembly of FIG. 14.
FIG. 15B is a cross-sectional view taken along line 15B-15B of FIG. 15A.

Referring to FIGS. 14 and 17, the passage body 420 can have an elongated rectangular shape with a first end 420a and a second end 420b. A central opening 422 extends through the passage body 420 from the first end 420a to the second end 420b along a longitudinal axis A of the passage body 420. The central opening 422 is dimensioned to allow the plunger 410 to move axially therein.

An outlet channel 442 and an inlet channel 444 also extend axially within the passage body 420, from the first end 420a of the passage body 420. Meanwhile, a first port channel 446 and a second port channel 448 extend axially within the body from the second end 420b of the passage body 420. As shown, the outlet channel 442, the inlet channel 444 and the first and second port channels 446, 448 are distributed about the longitudinal axis A of the body, running parallel thereto. In the embodiment illustrated, the outlet channel 442, the inlet channel 444 and the first and second port channels 446, 448 are located adjacent to respective corners of the rectangular passage body 420.

Figure 18A:
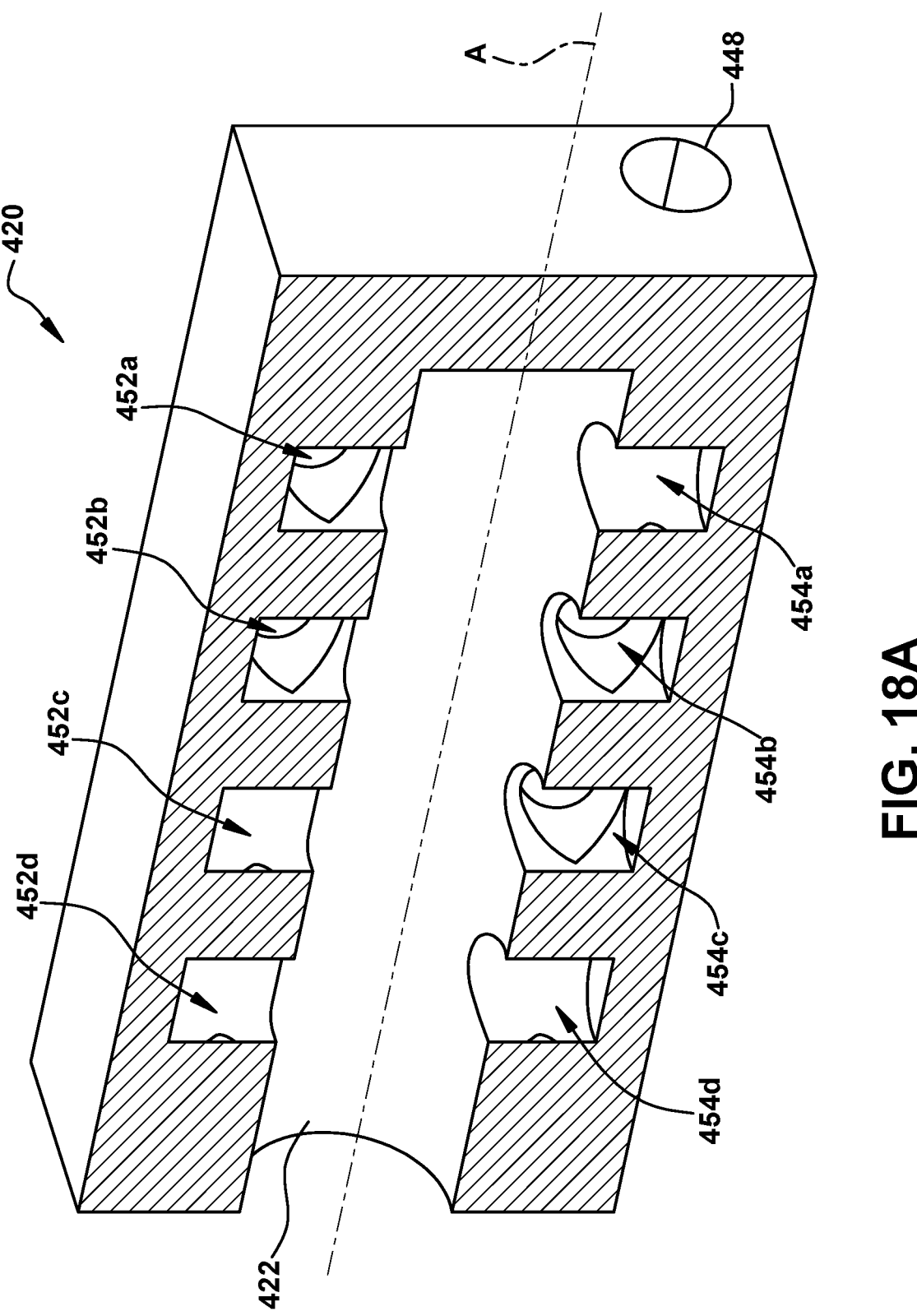
FIG. 18A is cross-sectional view taken along line 18A-18A of FIG. 17.
Figures 18B, 18C:
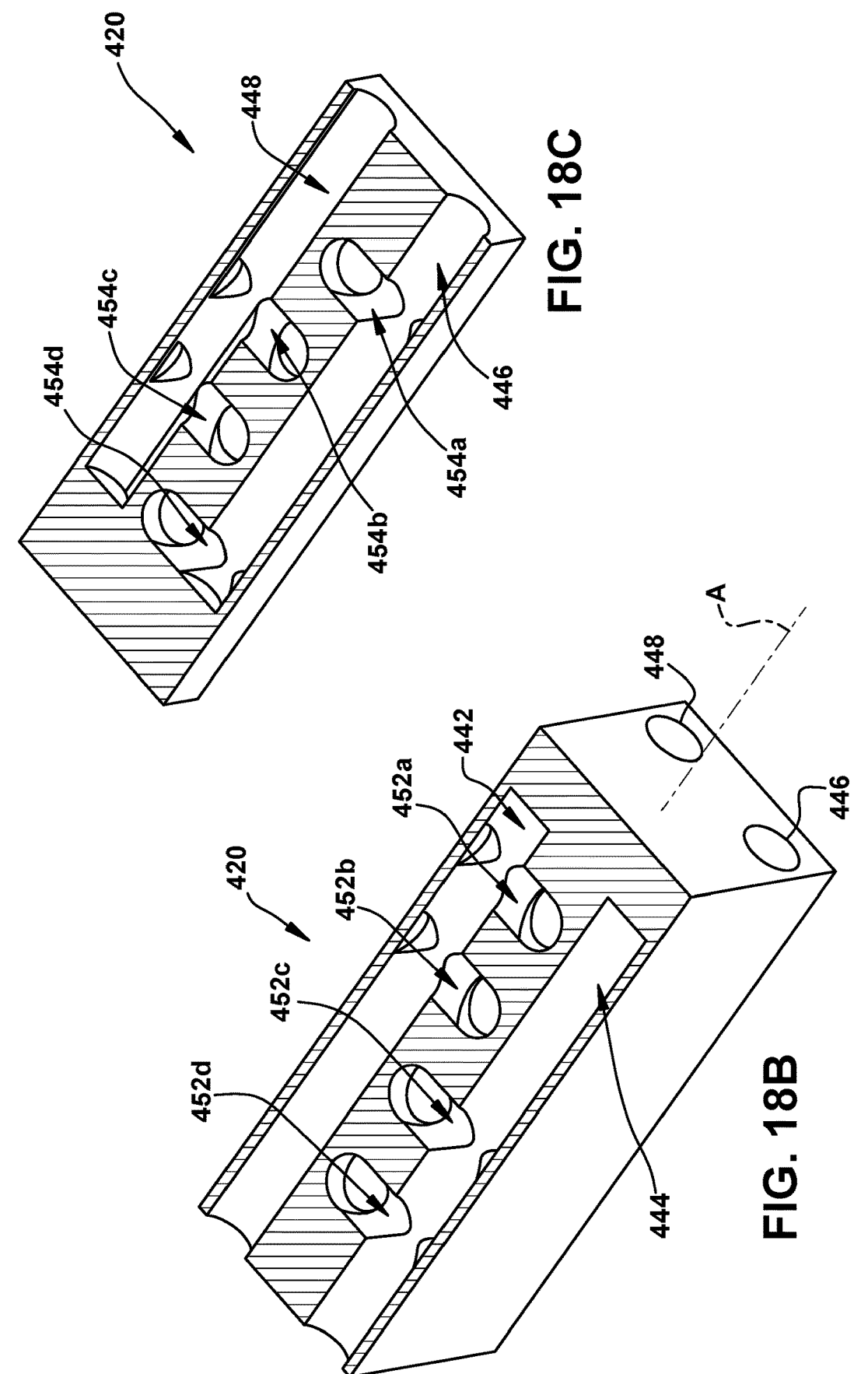
FIG. 18B is a cross-sectional view taken along line 18B-18B of FIG. 17.
FIG. 18C is a cross-sectional view taken along line 18C-18C of FIG. 17.

Referring to FIG. 18B, first and second upper connecting passages 452a, 452b fluidly connect the central opening 422 to the outlet channel 442. Third and fourth upper connecting passages 452c, 452d fluidly connect the central opening 422 to the inlet channel 444. In the embodiment illustrated, the upper connecting passages 452a, 452b, 452c, 452d are circular passages that each includes a vertical portion (see, FIG. 18A) and a horizontal portion (see, FIG. 18B). It is contemplated that the upper connecting passages 452a, 452b, 452c, 452d can have other cross-sectional shapes, e.g. rectangular, or be straight passages.

Referring to FIG. 18C. a first lower connecting passage 454a and a fourth lower connecting passage 454d fluidly connect the central opening 422 to the first port channel 446. A second lower connecting passage 454b and a third lower connecting passage 454c fluidly connect the central opening 422 to the second port channel 448. In the embodiment illustrated, the lower connecting passages 454a, 454b, 454c, 454d are circular passages that each includes a vertical portion (see, FIG. 18A) and a horizontal portion (see, FIG. 18C). It is contemplated that the lower connecting passages 454a, 454b, 454c, 454d can have other cross-sectional shapes, e.g. rectangular, or be straight passages.

Referring to FIGS. 14-15B, an adapter 405 is positioned between the passage body 420 and the upper chamber body 142. The adapter 405 includes a first through hole 406 and a second through 407 that extend from an upper surface 405a to a lower surface 405b. When the adapter 405 is positioned between the passage body 420 and the upper chamber body 142, the first through hole 406 is positioned and dimensioned to fluidly connect the second port channel 448 (which is open to the second end 420b of passage body 420) to the through hole 156 in the upper chamber body 142. Meanwhile, the second through hole 407 is positioned and dimensioned to fluidly connect the first port channel 446 (also open to the second end 420b of the passage body 420) to the upper passage outlet 152 of the upper chamber body 142. In the embodiment illustrated (see, FIG. 15B), the second through hole 407 of adapter 405 takes the form of an S-shaped passage passage for allowing its opening in the upper surface 405a to be offset from its opening in the lower surface 405b.

Referring to FIG. 14, an actuator 460, e.g. a solenoid or a motor, is attached to the first end 420a of the passage body 420. The actuator 460 is configured to engage an end of the plunger 410 to move the plunger 410, as described in detail below. It is contemplated that the actuator 460 may include a rod (not shown) that applies a force to the end of the plunger 410 to push the plunger 410 in one direction, e.g. against the action of a counter-spring 462 in order to achieve reciprocation of the plunger. Alterantively, the actuator 460 may be connected to the end of the plunger 410 (e.g. threaded thereto) such that the actuator 460 may actively move the plunger 410 in two, opposing axial directions in a reciprocating fashion.

Figures 19, 20:
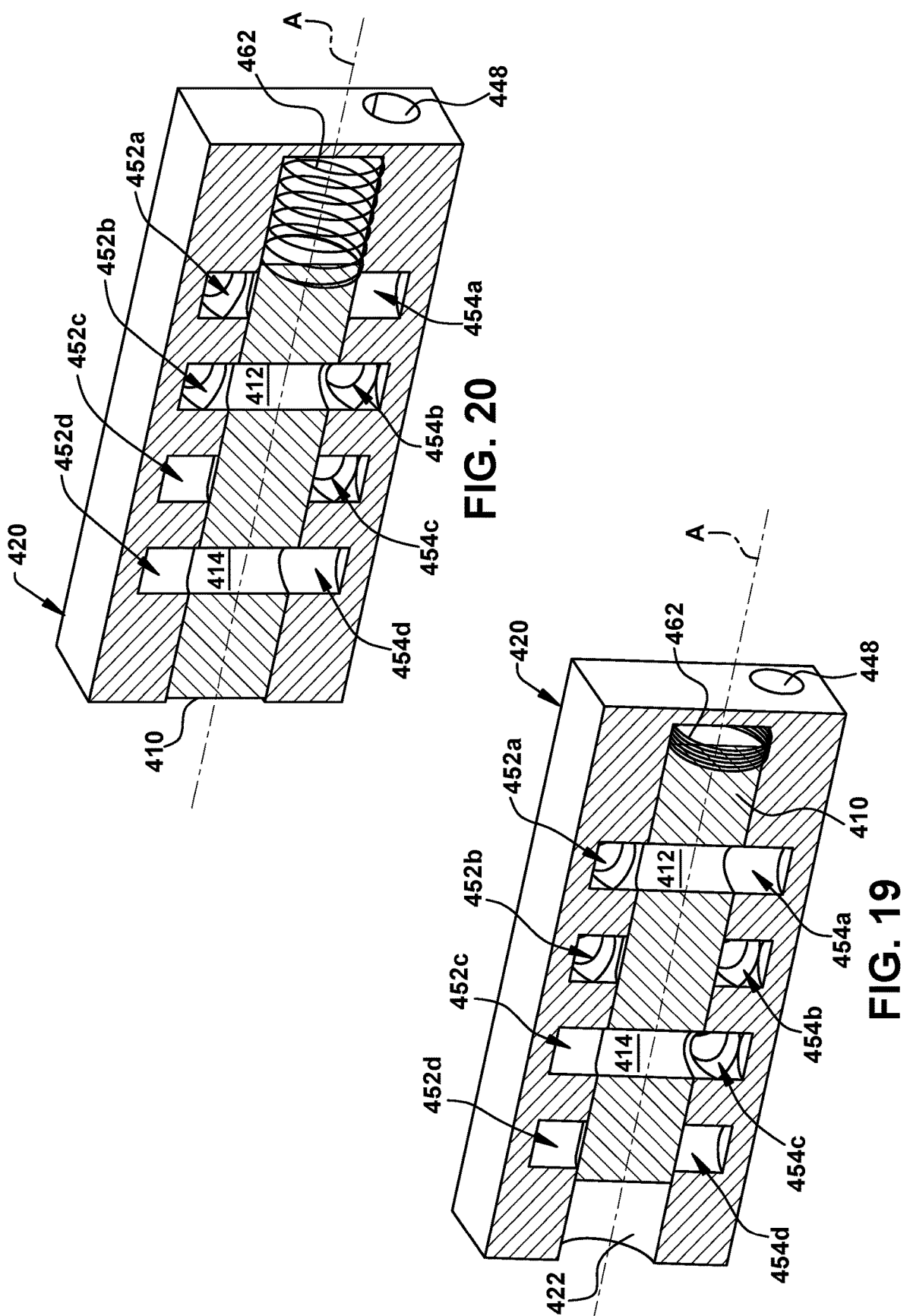
FIG. 19 is a cross-sectional view of the pump assembly of FIG. 14 taken along line 19-19 of FIG. 14 and showing the plunger in a first actuation state.
FIG. 20 is a cross-sectional view as in FIG. 19, but with the plunger in a second actuation state.

Referring to FIGS. 19 and 20, the plunger 410 is posi-tioned in the central opening 422 and is configured to move between a first actuation state (FIG. 19) and a second actuation state (FIG. 20). When in the first actuation state, the first through hole 412 in the plunger fluidly connects the first upper connecting passage 452a to the first lower con-necting passage 454a, and the second through hole 414 in the plunger fluidly connects the third upper connecting passage 452c to the third lower connecting passage 454c. When in the second actuation state, the first through hole 412 in the plunger fluid connects the second upper connect-ing passage 452b to the second lower connecting passage 454b, and the second through hole 414 in the plunger fluidly connects the fourth upper connecting passage 452d to the fourth lower connecting passage 454d. The actuator 460 drives the plunger 410 between the first position (FIG. 19) and the second position (FIG. 20).

In one embodiment, a spring 462 (FIGS. 19 and 20) is positioned between an end of the plunger 410 and an end of the central opening 422. The spring 462 is configured to bias the plunger 410 to the second actuation state (FIG. 20). The spring 462 may assist the actuator 460 in returning the plunger 410 to the second actuation state or the spring 462 may provide the sole force to push the plunger 410 to the second actuation state.

The plunger assembly 400 will now be described in relation to a mode of operation. Referring to FIG. 14, the opening of the inlet channel 444 in the first end 420a of the passage body is attachable to the drain line 54 (FIG. 1), which in turn is connected to the catheter 52. The opening of the outlet channel 442 in the first end 420a is attached to the second line 56 (FIG. 1), which in turn is connected to the reservoir 80. As noted above, the bag/pouch 82 is configured to have a slight vacuum. In this manner, upon connection with the plunger assembly 400 a predetermined suction is applied to the outlet channel 442 of the plunger assembly 400.

The passage body 420, the adapter 405 and the upper chamber body 142 are dimensioned so that when they are assembled together, the first port channel 446 of the passage body 420, the second through hole 407 of the adapter 405 and the upper passage outlet 152 of the upper chamber body 142 are in fluid communication with each other. As described in detail above, the upper passage outlet 152 fluidly communicates with the second chamber cavity 158B (FIG. 9). Accordingly, fluid entering the first port channel 446 communicates with the second chamber cavity 158B. Similarly, the second port channel 448 of the passage body 420, the first through hole 406 of the adapter 405 and the through hole 156 of the upper chamber boy 142 are in fluid communication with each other. As described in detail above, the through hole 156 fluidly communicates with the first chamber cavity 158A (FIG. 9). Accordingly, fluidly entering the second port channel 448 communicates with the first chamber cavity 158A.

Referring to FIG. 19 (wherein the actuator is removed for clarity), the operation of the plunger assembly 400 will be described with the plunger 410 starting in the first actuation state. In the first actuation state, the second through hole 414 in the plunger 410 provides fluid communication between the third upper connecting passage 452c and the third lower connecting passage 454c, and by extension between the inlet channel 444 and the second port channel aaa448. As described above, the second port 448 fluidly communicates with the first chamber cavity 158A (FIG. 9), via the first through hole 406 and the through hole 156. It will be seen that when the plunger 410 is in the first actuation state ultimately the catheter 52 (connected to the inlet channel 444) is placed in fluid communication with the first chamber cavity 158A.

In the first actuation state, the first through hole 412 in the plunger 410 provides fluid communication between the first upper connecting passage 452a and the first lower connecting passage 454a of the passage body 420, and by extension between the outlet channel 442 and the first port channel 446. As described above, the first port channel 446 fluidly communicates with the second chamber cavity 158B (FIG. 9) via the second through hole 407 and the upper passage outlet 152. It will be seen that when the plunger 410 is in the first actuation state ultimately the reservoir 80 is placed in fluid communication with the second chamber cavity 158B.

As described in detail above, connecting the reservoir 80 (which is under negative pressure) with the second chamber cavity 158B causes the second chamber cavity 158B to contract as the first chamber cavity 158A expands. The expansion of the first chamber cavity 158A draws CSF from the patient 10 into the first chamber cavity 158A.

After a predetermined amount of time, the controller 90 can actuate the actuator 460 to move, i.e. translate, the plunger 410 to the second actuation state, illustrated in FIG. 20. In the second actuation state, the second through hole 414 of the plunger 410 establishes fluid communication between the fourth upper connecting passage 452d and the fourth lower connecting passage 454d, and by extension between the inlet channel 444 and the first port channel 446. In this respect, fluid communication is established between the catheter 52 (connected via the drain line 54 to the inlet channel 444) and the second chamber cavity 158B (connected to the first port 446).

Also, in the second actuation state, the first through hole 412 of the plunger 410 establishes fluid communication between the second upper connecting chamber 452b and the second lower connecting chamber 454b, and by extension between the outlet channel 442 and the second port channel 448. In this respect, fluid communication is established between the reservoir 80 (connected via the second line 56 to the outlet 442) and the first chamber cavity 158A (connected to the second port 448).

Once in this state, the second chamber cavity 158B expands as the first chamber cavity 158A contracts. The expansion of the second chamber cavity 158B draws CSF from the catheter 52 as the contraction of the first chamber cavity 158A forces CSF therein into the reservoir 80. The moving of the plunger 410 repeatedly between the first actuation state and the second actuation state causes the alternating connection of the reservoir 80 and the catheter 52 to the first chamber cavity 158A and the second chamber cavity 158B. The alternating connection is configured to controllably convey CSF from the patient 10 to the reservoir 80.

Although the invention has been described with respect to select embodiments, it shall be understood that the scope of the invention is not to be thereby limited, and that it instead shall embrace all modifications and alterations thereof coming within the spirit and scope of the appended claims.

What is claimed is:

1. A valve assembly for controlled drainage or delivery of a fluid from or to a patient, the valve assembly comprising:
   an outlet;
   an inlet;
   a diaphragm chamber;
   a diaphragm dividing the diaphragm chamber into a first chamber cavity and a second chamber cavity, the diaphragm being deflectable toward a first wall of the diaphragm chamber wherein the first chamber cavity contracts and the second chamber cavity expands, and oppositely toward a second wall of the diaphragm chamber wherein the second chamber cavity contracts and the first chamber cavity expands; and
   a plunger translatable between:
      a first actuation state that establishes fluid communication between the outlet and the second chamber cavity, and separately between the inlet and the first chamber cavity, and
      a second actuation state that establishes fluid communication between the outlet and the first chamber cavity, and separately between the inlet and the second chamber cavity,
   wherein said first chamber cavity and said second chamber cavity are fluidically isolated from one another in all actuation states of said plunger, and
   wherein the establishment of fluid communication during the first actuation state and during the second actuation state is independent of said diaphragm.

2. The valve assembly according to claim 1, wherein the plunger is configured to be successively translated between the first actuation state and the second actuation state, wherein the fluid communication established by the plunger in the first actuation state allows fluid to be drawn from the patient or from a pressurized supply reservoir up to a maximum volume of the first chamber cavity and wherein the fluid communication established by the plunger in the second actuation state allows fluid to be drawn from the patient or the pressurized supply reservoir up to a maximum volume of the second chamber cavity.

3. The valve assembly according to claim 2, said maximum volume of the first chamber cavity being equal to said maximum volume of the second chamber cavity, the maximum volume of said first chamber cavity being achieved by deflecting said diaphragm against said second wall of said diaphragm chamber and the maximum volume of said second chamber cavity being achieved by deflecting said diaphragm against said first wall of said diaphragm chamber.

4. The valve assembly according to claim 1, wherein when the plunger is in the first actuation state, movement of the diaphragm toward the second wall causes fluid accumulated in the second chamber cavity to exit through the outlet while fluid is drawn into the first chamber cavity through the inlet, and wherein when the plunger is in the second actuation state, movement of the diaphragm toward the first wall causes fluid in the first chamber cavity to exit through the outlet while fluid is drawn into the second chamber cavity through the inlet.

5. The valve assembly of claim 1, further comprising:
an actuator for translating the plunger; and
a controller for controlling operation of the actuator,
wherein the actuator engages a first end of the plunger and is adapted to move the plunger from said first actuation state to said second actuation state.

6. The valve assembly of claim 5, further comprising:
a spring attached to an opposite second end of the plunger for biasing the plunger toward said first actuation state.

7. A fluid drainage system for controlled drainage of a fluid from a patient, the system comprising:
the valve assembly of claim 1;
a drain line fluidly connected between the patient and said inlet for draining fluid from the patient; and
a collection reservoir fluidly connected to said outlet for collecting the fluid drained from the patient,
wherein when the plunger is in the first actuation state, movement of the diaphragm toward the second wall causes fluid accumulated in the second chamber cavity to exit through the outlet and to accumulate in the collection reservoir while fluid from the patient is drawn into the first chamber cavity via the drain line through the inlet, and wherein when the plunger is in the second actuation state, movement of the diaphragm toward the first wall causes fluid in the first chamber cavity to exit through the outlet and to accumulate in the collection reservoir while fluid from the patient is drawn into the second chamber cavity via the drain line through the inlet.

8. The fluid drainage system of claim 7, further comprising:
an actuator for translating the plunger; and
a controller for controlling operation of the actuator,
wherein the actuator engages a first end of the plunger and is adapted to move the plunger from said first actuation state to said second actuation state, and wherein said valve assembly, said actuator and said controller are integrated together in a compact portable pump assembly that can be worn or carried by an ambulatory patient.

9. The fluid drainage system of claim 7, further comprising a vacuum drawn against said outlet that tends to deflect the diaphragm toward the second wall in the first actuation state of said plunger and tends to deflect the diaphragm toward the first wall in the second actuation state of said plunger.

10. The fluid drainage system of claim 9, said collection reservoir comprising an expandable bag in fluid communication with said outlet, wherein expansion of said expandable bag supplies said vacuum drawn against said outlet.

11. The fluid drainage system of claim 10, further comprising and an expandable member disposed within the expandable bag of said collection reservoir, said expandable member having an expansion bias that presses against an interior wall of said expandable bag and thereby tends to expand a volume of said expandable bag.

12. The valve assembly according to claim 1, wherein in the first actuation state, the plunger blocks fluid communication between the outlet and the first chamber cavity and blocks fluid communication between the inlet and the second chamber cavity, and wherein in the second actuation state, the plunger blocks fluid communication between the outlet and the second chamber cavity and blocks fluid communication between the inlet and the first chamber cavity.

13. The valve assembly according to claim 1, wherein the diaphragm chamber is the only diaphragm chamber of the valve assembly.

14. The valve assembly according to claim 1, wherein the plunger is the only plunger of the valve assembly that is translatable between the first actuation state and the second actuation state.

15. The valve assembly according to claim 1, wherein the plunger is not connected to the diaphragm.

16. The valve assembly according to claim 1, wherein the plunger comprises through holes, wherein when the plunger is in the first actuation state, the through holes fluidly connect the outlet to the second chamber cavity and fluidly connect the inlet to the first chamber cavity to establish the fluid communication, and wherein when the plunger is in the second actuation state, the through holes fluidly connect the outlet to the first chamber cavity and fluidly connect the inlet to the second chamber cavity to establish the fluid communication.

17. A valve assembly for controlled drainage or delivery of a fluid from or to a patient, the valve assembly comprising:
a diaphragm disposed in a diaphragm chamber and dividing the diaphragm chamber into a first chamber cavity and a second chamber cavity, the diaphragm being deflectable toward a first wall of the diaphragm chamber to contract the first chamber cavity and expand the second chamber cavity, and oppositely toward a second wall of the diaphragm chamber to contract the second chamber cavity and expand the first chamber cavity;
a body having a central chamber, first and second upper connecting passages fluidly connecting the central chamber to an outlet of the body, third and fourth upper connecting passages fluidly connecting the central chamber to an inlet of the body, first and fourth lower connecting passages fluidly connecting the central chamber to a first port of the body, second and third lower connecting passages fluidly connecting the central chamber to a second port of the body, the first port fluidly connected to first chamber cavity and the second port fluidly connected to the second chamber cavity; and
a plunger disposed in the central chamber and translatable within the central chamber between:
a first actuation state that establishes fluid communication between the first upper connecting passage and the first lower connecting passage, and separately between the third upper connecting passage and the third lower connecting passage, and a second actuation state that establishes fluid communication between the second upper connecting passage and the second lower connecting passage, and separately between the fourth upper connecting passage and the fourth lower connecting passage, wherein said first chamber cavity and said second chamber cavity are fluidically isolated from one another in all actuation states of said plunger.

18. The valve assembly of claim 17, further comprising:

a first diaphragm body having formed as a recess in an upper surface thereof said first wall of the diaphragm chamber; and a second diaphragm body having formed as a recess in a lower surface thereof said second wall of the diaphragm chamber, wherein the upper surface of the first diaphragm body is disposed in registry with the lower surface of the second diaphragm body such that the first wall and the second wall define and enclose said diaphragm chamber.

19. The valve assembly according to claim 17, wherein the plunger is configured to be successively actuated between the first actuation state and the second actuation state, wherein the fluid communication established by the plunger in the first actuation state allows fluid to be drawn from the patient up to a maximum volume of the first chamber cavity, and wherein the fluid communication established by the plunger in the second actuation state allows fluid to be drawn from the patient up to a maximum volume of the second chamber cavity.

20. The valve assembly according to claim 19, said maximum volume of the first chamber cavity being equal to said maximum volume of the second chamber cavity, the maximum volume of said first chamber cavity being achieved by deflecting said diaphragm against said second wall of said diaphragm chamber and the maximum volume of said second chamber cavity being achieved by deflecting said diaphragm against said first wall of said diaphragm chamber.

21. The valve assembly according to claim 17, the plunger including a first through hole and a second through hole, wherein the first through hole fluidly connects the first upper connecting passage to the first lower connecting passage, and separately the second through hole fluidly connects the third upper connecting passage to the third lower connecting passage in the first actuation state, and wherein the first through hole fluidly connects the second upper connecting passage to the second lower connecting passage, and separately the second through hole fluidly connects the fourth upper connecting passage to the fourth lower connecting passage in the second actuation state.

22. A fluid delivery system for controlled delivery of a fluid to a patient, the system comprising:

the valve assembly of claim 17;

a supply line fluidly connected between the patient and said outlet for delivering fluid to the patient; and a pressurized supply reservoir fluidly connected to said inlet for supplying the fluid to the patient, wherein when the plunger is in the first actuation state, movement of the diaphragm toward the second wall causes fluid accumulated in the second chamber cavity to exit through the outlet and to flow to the patient while fluid in the pressurized supply reservoir is forced into the first chamber cavity via the supply line through the inlet, and wherein when the plunger is in the second actuation state, movement of the diaphragm toward the first wall causes fluid in the first chamber cavity to exit through the outlet and to be supplied to the patient while fluid from the pressurized supply reservoir is forced into the second chamber cavity via the supply line through the inlet.

23. The fluid delivery system of claim 22, further comprising a pressurized fluid forced against said outlet that tends to deflect the diaphragm toward the first wall in the first actuation state of said plunger and tends to deflect the diaphragm toward the second wall in the second actuation state of said plunger.

* * * * *